(12) United States Patent
Chestek et al.

(10) Patent No.: US 10,314,725 B2
(45) Date of Patent: Jun. 11, 2019

(54) METHOD FOR AMPLIFYING SIGNALS FROM INDIVIDUAL NERVE FASCICLES

(71) Applicant: THE REGENTS OF THE UNIVERSITY OF MICHIGAN, Ann Arbor, MI (US)

(72) Inventors: Cynthia Anne Chestek, Ann Arbor, MI (US); Melanie G. Urbanchek, Ann Arbor, MI (US); Paul S. Cederna, Milan, MI (US); Richard Brent Gillespie, Ann Arbor, MI (US); Nicholas B. Langhals, Ypsilanti, MI (US); Zachary Irwin, Ann Arbor, MI (US); Daniel C. Ursu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 95 days.

(21) Appl. No.: 14/940,703

(22) Filed: Nov. 13, 2015

(65) Prior Publication Data

US 2016/0143751 A1    May 26, 2016

Related U.S. Application Data

(60) Provisional application No. 62/079,206, filed on Nov. 13, 2014.

(51) Int. Cl.
*A61F 2/72* (2006.01)
*A61F 2/58* (2006.01)
(Continued)

(52) U.S. Cl.
CPC .............. *A61F 2/72* (2013.01); *A61F 2/583* (2013.01); *A61F 2002/5058* (2013.01);
(Continued)

(58) Field of Classification Search
CPC ........................................................ A61F 2/72
See application file for complete search history.

(56) References Cited

U.S. PATENT DOCUMENTS

| 4,030,141 A | * | 6/1977 | Graupe | ..................... | A61F 2/68 |
| | | | | | 623/25 |
| 4,341,221 A | | 7/1982 | Testerman | | |

(Continued)

FOREIGN PATENT DOCUMENTS

| EP | 1001827 A1 | 5/2000 |
| EP | 1312303 A2 | 5/2003 |

(Continued)

OTHER PUBLICATIONS

International Search Report and Written Opinion of the ISA for PCT/US2012/021311, ISA/KR, dated Aug. 29, 2012.
(Continued)

*Primary Examiner* — Bruce E Snow
*Assistant Examiner* — Melissa A Hoban
(74) *Attorney, Agent, or Firm* — Harness, Dickey & Pierce, P.L.C.

(57) ABSTRACT

The present disclosure provides methods and systems for receiving, with processing circuitry of an implant device, an electrical signal from a free tissue graft attached to a portion of a nerve (e.g., a nerve branch or fascicle) through an electrical conductor in electrical communication with the free tissue graft (e.g., muscle graft), the nerve having reinnervated the free tissue graft. The electrical signal from the free tissue graft has a voltage amplitude of greater than or equal to about 150 microvolts. The processing circuitry stores signal data corresponding to the electrical signal from the free tissue graft in a memory accessible to the processing circuitry.

18 Claims, 19 Drawing Sheets

(51) Int. Cl.
  *A61F 2/50* (2006.01)
  *A61F 2/68* (2006.01)
  *A61F 2/70* (2006.01)
  *A61F 2/76* (2006.01)

(52) U.S. Cl.
  CPC .............. *A61F 2002/5064* (2013.01); *A61F 2002/6827* (2013.01); *A61F 2002/6872* (2013.01); *A61F 2002/701* (2013.01); *A61F 2002/704* (2013.01); *A61F 2002/7635* (2013.01)

(56) References Cited

U.S. PATENT DOCUMENTS

| | | |
|---|---|---|
| 4,585,652 A | 4/1986 | Miller et al. |
| 4,662,884 A | 5/1987 | Stensaas et al. |
| 5,031,621 A | 7/1991 | Grandjean et al. |
| 5,092,332 A | 3/1992 | Lee et al. |
| 5,130,412 A | 7/1992 | Wellinghoff et al. |
| 5,178,161 A * | 1/1993 | Kovacs ............ A61B 17/1128 600/373 |
| 5,368,028 A | 11/1994 | Palti |
| 5,513,636 A | 5/1996 | Palti |
| 5,540,734 A | 7/1996 | Zabara |
| 6,095,148 A | 8/2000 | Shastri et al. |
| 6,132,752 A | 10/2000 | Pickett et al. |
| 6,179,835 B1 | 1/2001 | Panescu et al. |
| 6,190,893 B1 | 2/2001 | Shastri et al. |
| 6,197,881 B1 | 3/2001 | Cosnier |
| 6,294,245 B1 | 9/2001 | Roitman et al. |
| 6,331,244 B1 | 12/2001 | Lewis et al. |
| 6,448,076 B2 | 9/2002 | Dennis et al. |
| 6,468,304 B1 | 10/2002 | Dubois-Rande et al. |
| 6,569,654 B2 | 5/2003 | Shastri et al. |
| 6,627,154 B1 | 9/2003 | Goodman et al. |
| 6,696,575 B2 | 2/2004 | Schmidt et al. |
| 6,730,212 B1 | 5/2004 | Yamagishi et al. |
| 6,890,715 B1 | 5/2005 | Lewis et al. |
| 7,045,205 B1 | 5/2006 | Sager |
| 7,070,592 B2 | 7/2006 | Santini, Jr. et al. |
| 7,120,486 B2 | 10/2006 | Leuthardt et al. |
| 7,147,865 B2 | 12/2006 | Fishman et al. |
| 7,181,288 B1 | 2/2007 | Rezai et al. |
| 7,233,097 B2 | 6/2007 | Rosenthal et al. |
| 7,708,908 B2 | 5/2010 | Kim et al. |
| 8,005,526 B2 | 8/2011 | Martin et al. |
| 8,180,461 B2 | 5/2012 | Mamo et al. |
| 8,353,897 B2 | 1/2013 | Doyle et al. |
| 8,676,334 B2 * | 3/2014 | Youn ................ A61N 1/36003 607/48 |
| 8,812,096 B2 * | 8/2014 | Flaherty ................ A61F 2/50 600/544 |
| 8,936,794 B2 | 1/2015 | Martin et al. |
| 9,044,347 B2 | 6/2015 | Cederna et al. |
| 9,352,146 B2 | 5/2016 | Langhals et al. |
| 2003/0097050 A1 | 5/2003 | Baru Fassio |
| 2005/0033132 A1 | 2/2005 | Shults et al. |
| 2005/0048651 A1 | 3/2005 | Ryttsen et al. |
| 2005/0121068 A1 | 6/2005 | Sager et al. |
| 2005/0234513 A1 | 10/2005 | Alexander et al. |
| 2005/0263394 A1 | 12/2005 | Lewis et al. |
| 2006/0057451 A1 | 3/2006 | Okuzaki et al. |
| 2006/0160100 A1 | 7/2006 | Gao et al. |
| 2007/0038311 A1 | 2/2007 | Kuiken et al. |
| 2007/0060815 A1 | 3/2007 | Martin et al. |
| 2007/0073130 A1 | 3/2007 | Finch et al. |
| 2008/0097280 A1 | 4/2008 | Martin et al. |
| 2008/0228240 A1 * | 9/2008 | Edell ................ A61B 5/04888 607/48 |
| 2009/0118806 A1 | 5/2009 | Vetter et al. |
| 2009/0292325 A1 | 11/2009 | Cederna et al. |
| 2010/0211172 A1 | 8/2010 | Bellamkonda et al. |
| 2011/0087315 A1 | 4/2011 | Richardson-Burns et al. |
| 2011/0257504 A1 | 10/2011 | Hendricks et al. |
| 2012/0101595 A1 * | 4/2012 | Jung ................ A61F 2/68 623/25 |
| 2012/0232630 A1 | 9/2012 | Daneshvar |
| 2013/0304174 A1 * | 11/2013 | Langhals ............ A61F 2/72 607/118 |
| 2014/0005763 A1 | 1/2014 | Cederna et al. |
| 2014/0249645 A1 | 9/2014 | Cederna et al. |
| 2014/0277588 A1 * | 9/2014 | Patt ................ A61F 2/586 623/57 |
| 2015/0173918 A1 * | 6/2015 | Herr ................ A61F 2/72 623/25 |
| 2016/0143751 A1 * | 5/2016 | Chestek ............ A61F 2/72 623/25 |

FOREIGN PATENT DOCUMENTS

| | | |
|---|---|---|
| WO | 97/16545 A1 | 5/1997 |
| WO | 2007/028003 | 3/2007 |
| WO | 2008/085199 | 7/2008 |
| WO | 2010/011386 A2 | 1/2010 |
| WO | 2011/127166 | 10/2011 |
| WO | 2012/097297 A2 | 7/2012 |

OTHER PUBLICATIONS

International Search Report for PCT/US2009/042342, ISA/KR, dated Feb. 5, 2010.
Baghmanli, Ziya et al., "Impact of PEDOT on Peripheral Nerve Regeneration and Muscle Reinnervation," Plastic and Reconstructive Surgery, 70A, p. 52 (Jun. 2010 supplement).
Kim, D., et al., "Conducting polymers grown in hydrogel scaffolds coated on neural prosthetic devices," (2004), J. Biomed. Mater. Res., 71A(4), pp. 577-585.
Murji, A., et al., "The Role of Intraoperative Frozen Section Histology in Obstetrical Brachial Plexus Reconstruction", J. Reconstr. Microsurg, 2008. 24(3): p. 203-9.
Nyberg, T., et al., Ion Conducting Polymer Microelectrodes for Interfacing with Neural Networks, Journal of Neuroscience Methods, vol. 160, 2007, pp. 16-25 (abstract only).
Egeland, Brent M., et al., "Poly(3,4-ethylenedioxythiophene) PEDOT Bioengineered Constructs Can Deliver Afferent SNAPs With High Efficiency," American Society of Peripheral Nerve Annual Meeting, Jan. 6-9, 2009, Maui, HI (Presentation).
Richardson-Burns, Sarah M. et al., "Electrochemical polymerization of conducting polymers in living neural tissue", J. Neural Eng. 4 (2007), L6-L13.
Abidian, M.R., et al., "Conducting-polymer nanotubes for controlled drug release," (2006), Advanced Materials, 18, pp. 405-409.
Abidian, Mohammad Reza, et al., "Experimental and Theoretical Characterization of Implantable Neural Microelectrodes Modified with Conducting Polymer Nanotubes," Biomaterials, vol. 29, 2008 (available online Dec. 18, 2008), p. 1273-1283.
Campbell, T.E., et al., "Incorporation of Erythrocytes into Polypyrrole to Form the Basis of a Biosensor to Screen for Rhesus (D) Blood Groups and Rhesus (D) Antibodies," (1999), Electroanalysis, vol. 11, No. 4, pp. 215-222.
Chew, S.Y., et al., "Sustained Release of Proteins from Electrospun Biodegradable Fibers," (2005), Biomacromolecules, 6, pp. 2017-2024.
Cui, et al., "Surface modification of neural recording electrodes with conducting polymer/biomolecule blends," (2001), J. Biomed. Mater. Res., vol. 56, No. 2, pp. 261-272.
Cui, X., et al., "Electrochemical deposition and characterization of conducting polymer polypyrrole/PSS on multichannel neural probes," (2001), Sensors and Actuators, A 93, pp. 8-18.
Cui, X., et al., "Electrochemical deposition and characterization of poly(3,4-ethylenedioxythiophene) on neural microelectrode arrays," (2003), Sensors and Actuators, B 89, pp. 92-102.
Cui, X., et al., "In vivo studies of polypyrrole/peptide coated neural probes," (2003), Biomaterials, 24, pp. 777-787.
DiPaolo, B.C., et al., "Nanofiber scaffolding for improved neural electrode biocompatability," (2003), IEEE 29th Annual Conference, pp. 21-22.

(56) References Cited

OTHER PUBLICATIONS

Dong, H., et al., "Sub-Micrometer Conducting Polyaniline Tubes Prepared from Polymer Fiber Templates," (2004), Chem. Mater., 16, pp. 371-373.
Ghosh, S., et al., "Electrochemical Characterization of Poly(3,4-ethylene dioxythiophene) Based Conducting Hydrogel Networks," (2000) Journal of the Electrochemical Society, vol. 147, No. 5, pp. 1872-1877.
Gilmore, K., et al., "Preparation of Hydrogel/Conducting Polymer Composites," (1994), Polymer Gels and Networks, 2, pp. 135-143.
Gooding, J.J., et al., "Electrochemical modulation of antigent-antibody binding," (2004), Biosensors and Bioelectronics, 20, pp. 260-268.
Khor, E., et al., "In situ polymerization of pyrrole in animal tissue in the formation of hybrid biomaterials," (1995), Biomaterials, vol. 16, No. 8, pp. 657-661.
Kim, et al., "Incorporation and controlled release of a hydrophilic antibiotic using poly(lactide-co-glycolide)-based electrospun nanofibrous scaffolds," (2004), Journal of Controlled Release, 98, pp. 47-56.
Kim, B.C., et al., "Electroformation of conducting polymers in a hydrogel support matrix," (2000), Polymer, 41, pp. 1783-1790.
Kim, B.H., et al., "Synthesis, characteristics, and field emission of doped and de-doped polypyrrole, polyaniline, poly (3,4-ethylenedioxythiophene) nanotubes and nanowires," (2005), Synthetic Metals, 150, pp. 279-284.
Kipke, D. R., et al., "Silicon-Substrate Intracortical Microelectrode Arrays for Long-Term Recording of Neuronal Spike Activity in Cerebral Cortex," (2003), IEEE Transactions on Neural Systems and Rehabilitation Engineering, vol. 11, No. 2, pp. 151-155.
Kositsky, M., et al., "Dynamical Dimension of a Hybrid Neurorobitic System," (2003), IEEE Transactions on Neural Systems and Rehabilitation Engineering, vol. 11, No. 2, only p. 155 available.
Nyberg, T., et al., "Polymer Hydrogel Microelectrodes for Neural Communication," (2002), Biomedical Microdevices vol. 4, No. 1, pp. 43-52.
Rahman, et al., "The biosensor based on the pyruvate oxidase modified conducting polymer for phosphate ions determinations," (2006), Biosensors and Bioelectronics, vol. 21, No. 7, pp. 1116-1124.
Egert, Daniel, et al., "New Class of Chronic Recording Multichannel Neural Probes With Post-Implant Self-Deployed Satellite Recording Sites," Solid-State Sensors, Actuators and Microsystems Conference (TRANSDUCERS), Proceedings from IEEE 16th International Conference, Jun. 5-9, 2011, pp. 958-961.
Schmidt, C.E., et al., "Stimulation of neurite outgrowth using an electrically conducting polymer," (Aug. 1997), Applied Biological Sciences: Proc. Natl. Acad. Sci. USA, vol. 94, pp. 8948-8953.
Woerly, S., "Restorative surgery of the central nervous system by means of tissue engineering using NeuroGel implants," (2000), Neurosurg Rev., 23, pp. 59-77.
Xiao, Y., et al., "Electrochemical polymerization of poly(hydroxymethylated-3,4-ethylenedioxythiophene) (PEDOT-MeOH) on multichannel neural probes," (2004), Sensors and Actuators, B 99, pp. 437-443.
Yang, J., et al., "Microporous conducting polymers on neural microelectrode arrays II Physical characterization," (2004), Sensors and Actuators, A 113, pp. 204-211.
Yang, J., et al., "Microporous conducting polymers on neural microelectrode arrays I. Electrochemical deposition," (2004), Sensors and Actuators, B 101, pp. 133-142.
Yang, J. et al., "Ordered surfactant-templated poly(3,4-ethylenedioxythiophene) (PEDOT) conducting polymer on microfabricated neural probes," (2005), Acta Biomaterialia, 1, pp. 125-136.
Zhang, Y., et al., "Recent development of polymer nanofibers for biomedical and biotechnological applications," (2005), Journal of Materials Science: Materials in Medicine, 16, pp. 933-946.
International Preliminary Report on Patentability dated Jul. 16, 2013 for PCT International Application No. PCT/US2012/021311 (Pub. No. WO 2012/097297).
International Preliminary Report on Patentability dated Nov. 2, 2010 for PCT International Application No. PCT/US2009/042342 (Pub. No. WO 2010/011386).
Abidian, M.R., et al., "Sensory Protection Recovery Follows Nerve Regeneration Through an Electrically Conducting Nerve Graft," 54th Annual Meeting, Plastic Surgery Research Council, May 27-30, 2009, Pittsburgh, PA, PSRC Abstract Supplement, vol. 126, No. 3 (Supplement), p. 40 (Jun. 2009) (Abstract only).
Aszmann, Oskar C., et al., "Evidence in Support of Collateral Sprouting After Sensory Nerve Resection," Annals of Plastic Surgery, vol. 37, No. 5, pp. 520-525 (1996).
Aszmann, Oskar C., et al., "Neuroma Prevention by End-to-Side Neurorraphy: An Experimental Study in Rats," Journal of Hand Surgery, vol. 28A, No. 6, pp. 1022-1028 (Nov. 2003).
Chandra, S., et al., "Proton-conducting gel electrolyte," Solid State Ionics, vol. 154-155, pp. 609-619 (2002).
Egeland, B.M., et al., "Biosynthetic Poly(3,4-ethylenedioxythiophene) (PEDOT) PNS Interfaces Can Deliver Afferent SNAPs With High Efficiency," American Society of Plastic Surgeons Meeting, Oct. 30-Nov. 6, 2008, Chicago, IL (Summary).
Egeland, B.M., et al., "Biosynthetic Poly(3,4-ethylenedioxythiophene) (PEDOT) PNS Interfaces Can Deliver Afferent SNAPs With High Efficiency," American Society for Peripheral Nerve Annual Scientific Meeting, Maui, HI, Jan. 11, 2009 (also presented at Annual Research Conference, Ann Arbor, MI, Mar. 2009) (Presentation).
Egeland, Brent M., et al., "In Vivo Electrical Conductivity across Critical Nerve Gaps Using Poly(3,4-ethylene-dioxythiophene)-Coated Neural Interfaces," Plastic and Reconstructive Surgery, vol. 126, No. 6, pp. 1865-1873 (Dec. 2010).
Egeland, Brent, et al., "In Vivo Electrophysiologic Properties of Poly 3,4-ethylene-dioxythiophene (PEDOT) in a Biosynthetic Nerve Interface," Midwestern Association of Plastic Surgeons, 48th Annual Scientific Meeting, May 4, 2008, Chicago, IL (Abstract and Presentation).
Egeland, Brent, et al., "In Vivo Electrophysiologic Properties of Poly (3,4-ethylene-dioxythiophene) PEDOT in Peripheral Motor Nerves," 54th Annual Meeting, Plastic Surgery Research Council, May 27-30, 2009, Pittsburgh, PA, PSRC Abstract Supplement, vol. 126, No. 3 (Supplement), p. 89 (Jun. 2009) (Abstract only).
Gao, Mei, et al., "Biosensors Based on Aligned Carbon Nanotubes Coated with Inherently Conducting Polymers," Electroanalysis, vol. 15, No. 13, pp. 1089-1094 (2003).
Herr, Hugh, "New Horizons for Orthotic & Prosthetic Technology," Materials Research Society Spring Meeting, Symposium U: Advanced Materials for Neuroprosthetic Interfaces, Session U9: Integrated Designs and Devices, Apr. 12, 2007, San Francisco, CA (Oral Presentation) (Abstract only).
Jadcherla, Yamini, et al., "Nerve Regeneration through PEDOT, an Electrically Conducting Polymer Nerve Graft," Plastic and Reconstructive Surgery, vol. 124, No. 4 Supplement, p. 67 (Oct. 2009).
Kim, Dong-Hwan, "Effect of Immobilized Nerve Growth Factor on Conductive Polymers: Electrical Properties and Cellular Response," Advanced Functional Materials, vol. 17, pp. 79-86 (2007) (published online Nov. 20, 2006).
Lebedev, Mikhail, et al., "Brain-machine interfaces: past, present and future," TRENDS in Neurosciences, vol. 29, No. 9, pp. 536-546 (2006) (published online Jul. 21, 2006).
Lock, John P., et al., "Electrochemical investigation of PEDOT films deposited via CVD for electrochromic applications," Synthetic Metals, vol. 157, pp. 894-898 (2007) (published online Oct. 29, 2007).
Peramo, Antonio, et al., "In Situ Polymerization of a Conductive Polymer in Acellular Muscle Tissue Constructs," Tissue Engineering: Part A, vol. 14, No. 3, pp. 423-432 (2008).
Pini, Niccolò, et al., "In situ growth of interdigitated electrodes made of polypyrrole for active fiber composites," Polymers for Advanced Technologies, vol. 18, pp. 249-253 (Mar. 2007) (published online Feb. 1, 2007).
Smela, Elisabeth, "Conjugated Polymer Actuators for Biomedical Applications," Advanced Materials, vol. 15, No. 6, pp. 481-494 (Mar. 17, 2003).

(56) References Cited

OTHER PUBLICATIONS

Spinks, Geoffrey M., et al., "Actuation behaviour of layered composites of polyaniline, carbon nanotubes and polypyrrole," Synthetic Metals, vol. 151, pp. 85-91 (2005) (published online Jun. 13, 2005).

Talbi, H., et al., "Electropolymerization of aniline on carbonized polyacrylonitrile aerogel electrodes: applications for supercapacitors," Journal of Applied Electrochemistry, vol. 33, pp. 465-473 (2003).

Urbanchek, M.G., et al., "A Tissue-Based Bioelectrical Interface With Reduced Impedance Compared to Copper Wire and Nerve," 54th Annual Meeting, Plastic Surgery Research Council, May 27-30, 2009, Pittsburgh, PA, PSRC Abstract Supplement, vol. 126, No. 3 (Supplement), p. 26 (Jun. 2009) (Abstract only).

Urbanchek, M.G., et al., "Myoblast and Nerve Compatibility with PEDOT an Intrinsically Conductive Material," American Society of Plastic Surgeons Meeting, Nov. 2008, Chicago, IL (Presentation).

Urbanchek, M.G., et al., "Nerve Regeneration Through an Electrically Conducting Polymer Nerve Graft," 54th Annual Vleeting, Plastic Surgery Research Council, May 27-30, 2009, Pittsburgh, PA, PSRC Abstract Supplement, vol. 126, No. 3 (Supplement), p. 90 (Jun. 2009) (Abstract only).

Watt, A.A.R., et al., "A PbS quantum-cube: conducting polymer composite for photovoltaic applications," Current Applied Physics, vol. 4, pp. 320-322 (2004).

Kuiken, TA. et al. "Targeted muscle reinnervation for real-time myoelectric control of multifunction artificial arms" Feb. 11, 2009 JAMA 301(6): 619-628.

M. Santhanalakshmi et al. "Implantable Neural Signal Amplifier for Epileptic Seizure Prediction" 2012 Procedia Engineering 38: 3426-3433.

Heiduschka, P., and S. Thanos. "Implantable bioelectronic interfaces for lost nerve functions." Progress in neurobiology 55.5 (1998): 433-461.

Borghi, T., Bonfanti, A., Gusmeroli, R., Zambra, G., and Spinelli, A.S. "A power-efficient analog integrated circuit for amplification and detection of neural signals" Aug. 20-25, 2008 Conf. Proc. IEEE Eng. Med. Biol. Soc.: 4911-5.

Kuiken, T. "Targeted reinnervation for improved prosthetic function" Feb. 2006 Phys. Med. Rehabil. Clin. N Am. (1): 1-13.

Kuiken, T.A.,et al. "The use of targeted muscle reinnervation for improved myoelectric prosthesis control in a bilateral shoulder disarticulation amputee" 2004 Prosthetics and Orthotics International 28: 245-253.

\* cited by examiner

Example: Recording amplified nerve signal data

Example: Control of prosthetic limb

Example: Decoding signals for control of prosthetic limb

Example: Monitoring nerves for pathological pain signals

Example: Monitoring pathological bladder contraction signals

Example: Stimulating nerves based on sensed pressure signals from a prosthetic device

METHOD FOR AMPLIFYING SIGNALS FROM INDIVIDUAL NERVE FASCICLES

CROSS-REFERENCE TO RELATED APPLICATIONS

This application claims the benefit of U.S. Provisional Application No. 62/079,206, filed on Nov. 13, 2014. The entire disclosure of the above application is incorporated herein by reference.

GOVERNMENT RIGHTS

This invention was made with government support under W911 NF-06-1-0218 awarded by the Army/ARO and N66001-11-C-4190 awarded by the Navy/SPAWAR. The Government has certain rights in the invention.

FIELD

The present disclosure relates to methods for amplifying signals from individual nerve fascicles and, more specifically, to methods for amplifying signals from individual nerve fascicles with implantable regenerative peripheral nerve interface devices and to systems and methods for receiving and processing the amplified signals.

BACKGROUND

This section provides background information related to the present disclosure which is not necessarily prior art.

There is a need to receive and record signals from nerves (for example, mammalian or human nerves) for subsequent processing and use in, for example, controlling prosthetic limbs, and/or in monitoring, diagnosing, and detecting conditions such as pathological pain signals, pathological contractions, tremor, spasticity, and the like, within an animal body and nervous system. Because of the inherently small size of many nerve fibers, especially of peripheral nerves, a nerve with an implanted electrode can develop scar tissue, which can represent a substantial fraction of the nerve and cause significant signal interference. Further, even without scarring, the signals detected by current systems utilizing sufficiently small electrodes are typically less than 100 microvolts, peak-to-peak ($\mu V$ pp) when recording from within the nerve and less than 10 $\mu V$ pp when recording from a cuff around the nerve. At these low levels, the signals detected by current systems are subject to significant noise and interference and can require significant, extensive hardware resources and processing power for detection, processing, and analysis of such signals.

SUMMARY

This section provides a general summary of the disclosure, and is not a comprehensive disclosure of its full scope or all of its features.

In various aspects, the present disclosure provides a method that includes receiving, with processing circuitry of an implant device, an electrical signal from a free tissue graft attached to a portion of a nerve, such as a nerve fascicle, through an electrical conductor in electrical communication with the free tissue graft, with the portion of the nerve having reinnervated the free tissue graft and the electrical signal from the free tissue graft having a voltage amplitude of greater than or equal to about 150 microvolts. In certain variations, the free tissue graft comprises muscular tissue.

The method also includes storing, with the processing circuitry, signal data corresponding to the electrical signal from the free tissue graft in a memory accessible to the processing circuitry.

In other variations, the present disclosure provides a system comprising an implant device having processing circuitry configured to receive an electrical signal from a free tissue graft attached to a portion of a nerve, such as a nerve fascicle, through an electrical conductor in electrical communication with the free tissue graft, and configured to store signal data corresponding to the electrical signal from the free tissue graft in a memory accessible to the processing circuitry, wherein the portion of the nerve has previously reinnervated the free tissue graft and the electrical signal from the free tissue graft has a voltage amplitude of greater than or equal to about 150 microvolts. In certain variations, the free tissue graft comprises muscular tissue.

In yet other variations, the present disclosure contemplates a method of amplifying a nerve signal in a subject. Such a method may comprise disposing a portion of a nerve within a free tissue graft and securing the portion of the nerve therein. Then, at least electrical conductor may be introduced into the free tissue graft. The at least one electrical conductor provides electrical communication with the nerve. The portion of the nerve regenerates within the free tissue graft so that the nerve produces an electrical signal of greater than or equal to about 150 microvolts without any external electrical input.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 14:
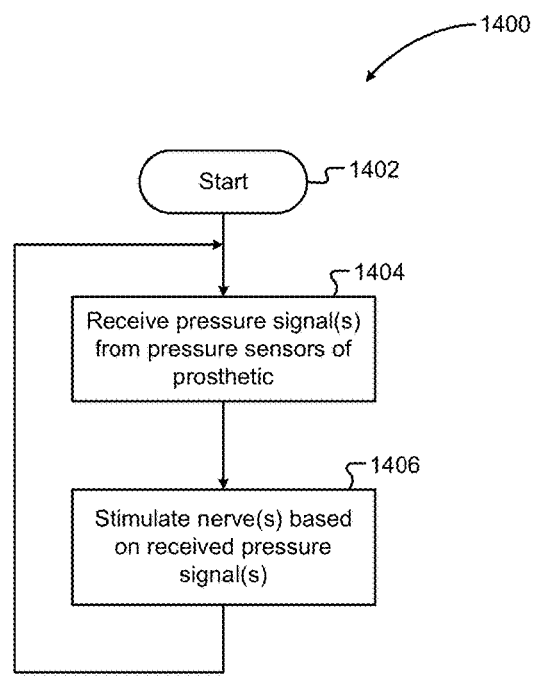

FIG. 14 a flowchart depicting an example control algorithm for stimulating nerves based on sensed pressure signal from a prosthetic device in accordance with certain aspects of the present disclosure.

Figure 15:
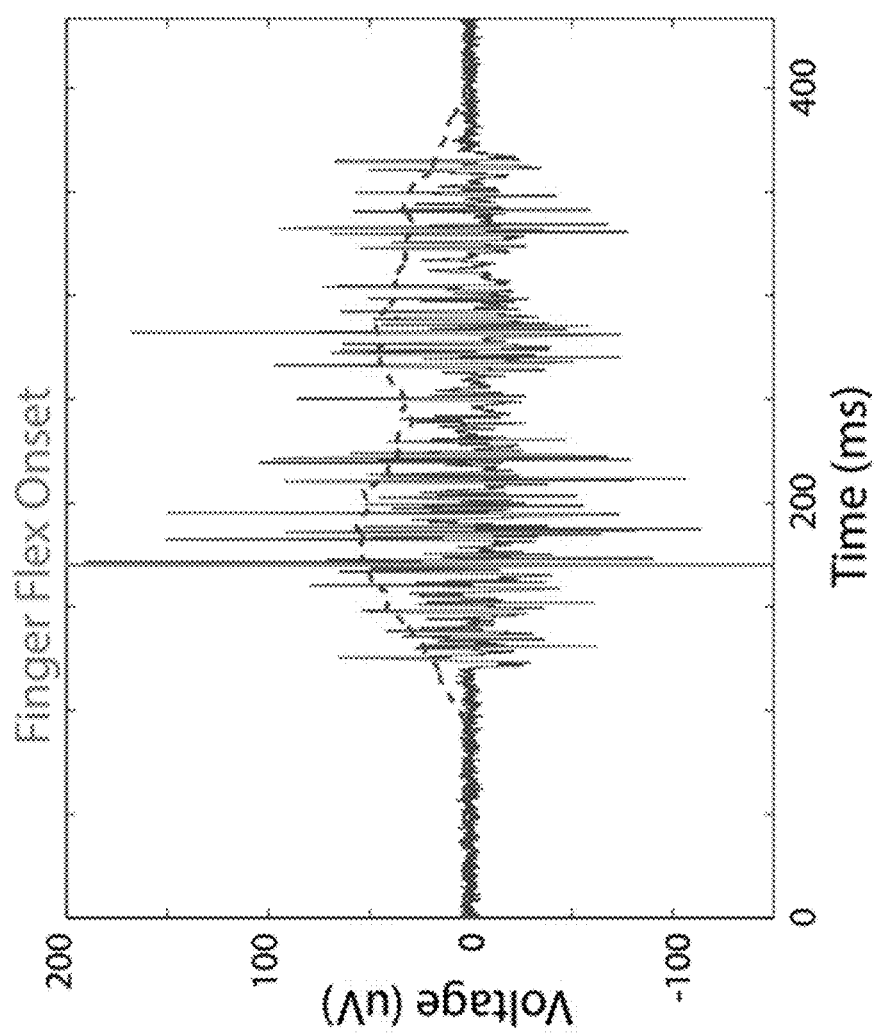

FIG. 15 is a graph showing nerve signal data corresponding to onset of a finger flexion movement.

Figure 16:
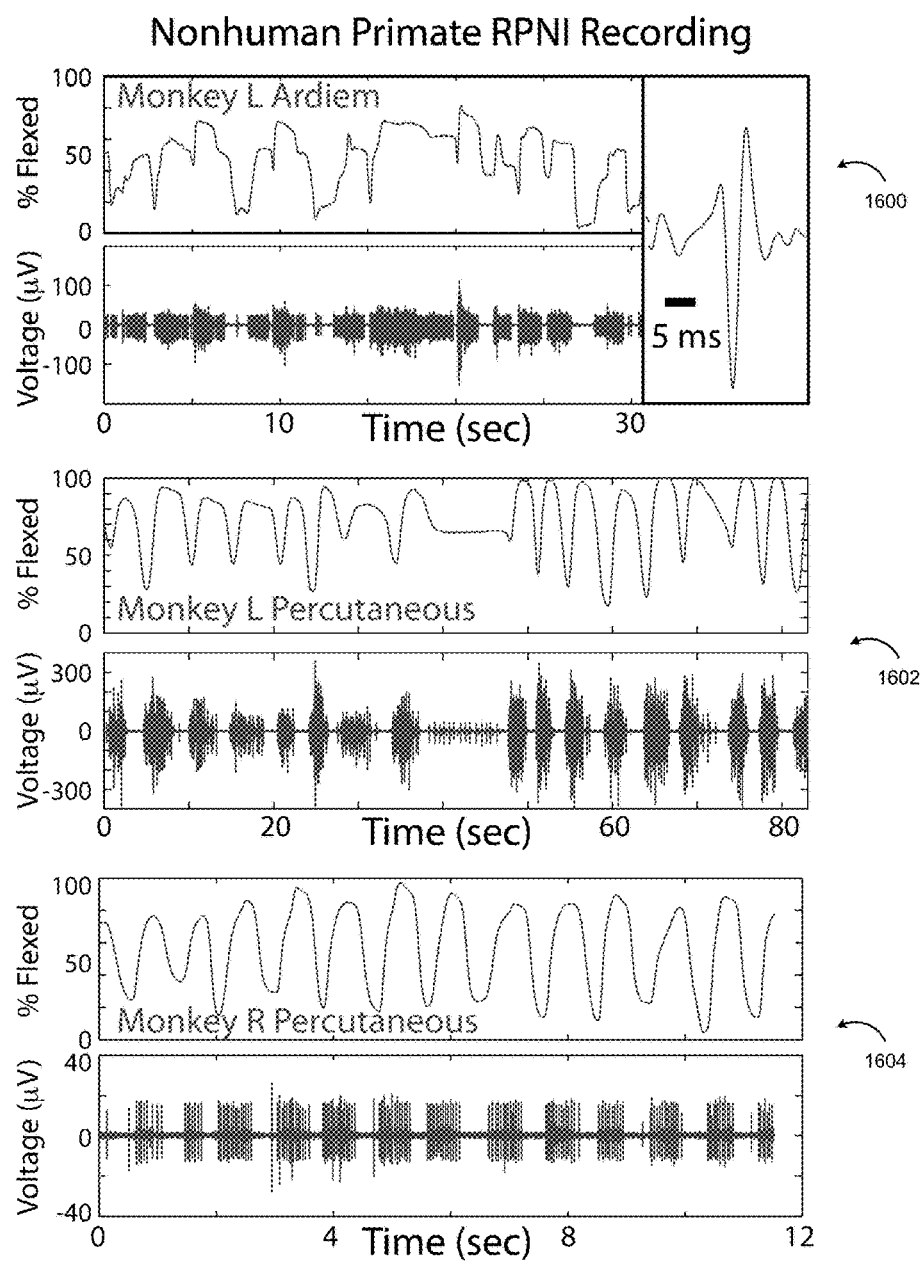

FIG. 16 is a group of graphs showing nerve signal data from implanted regenerative peripheral nerve interfaces.

Figure 17:
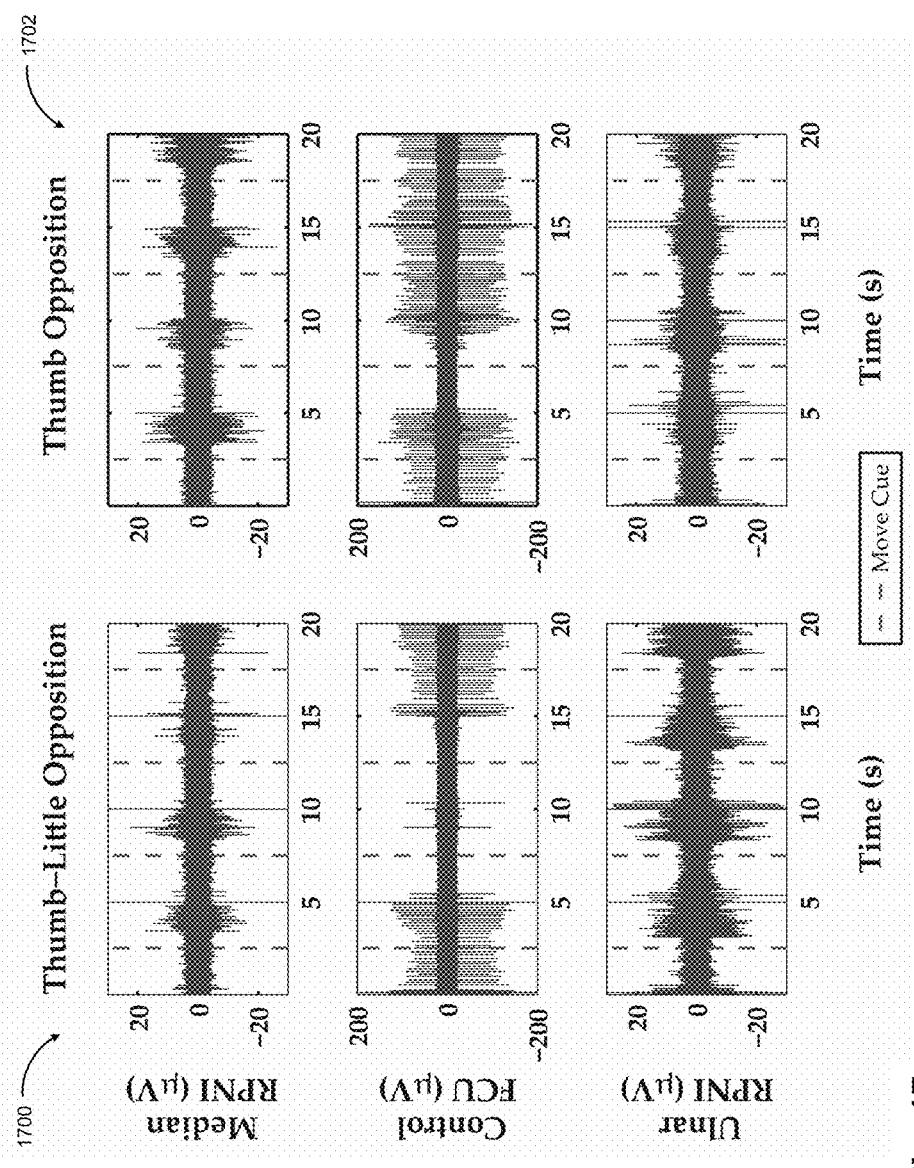

FIG. 17 is a group of graphs showing nerve signal data from implanted regenerative peripheral nerve interfaces and from a control muscle.

Figure 18:
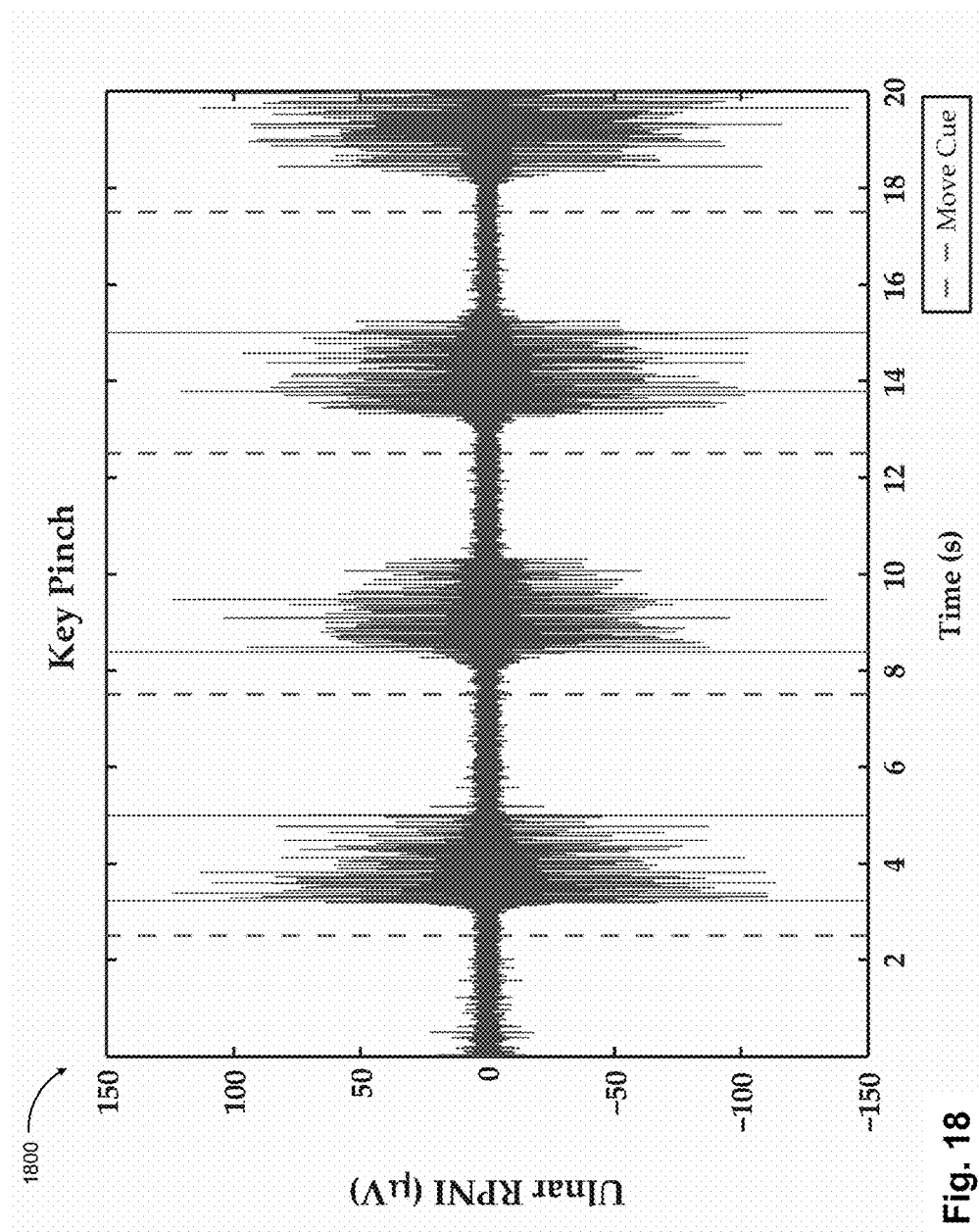

FIG. 18 is a graph showing nerve signal data from an implanted regenerative peripheral nerve interface.

Figure 19:
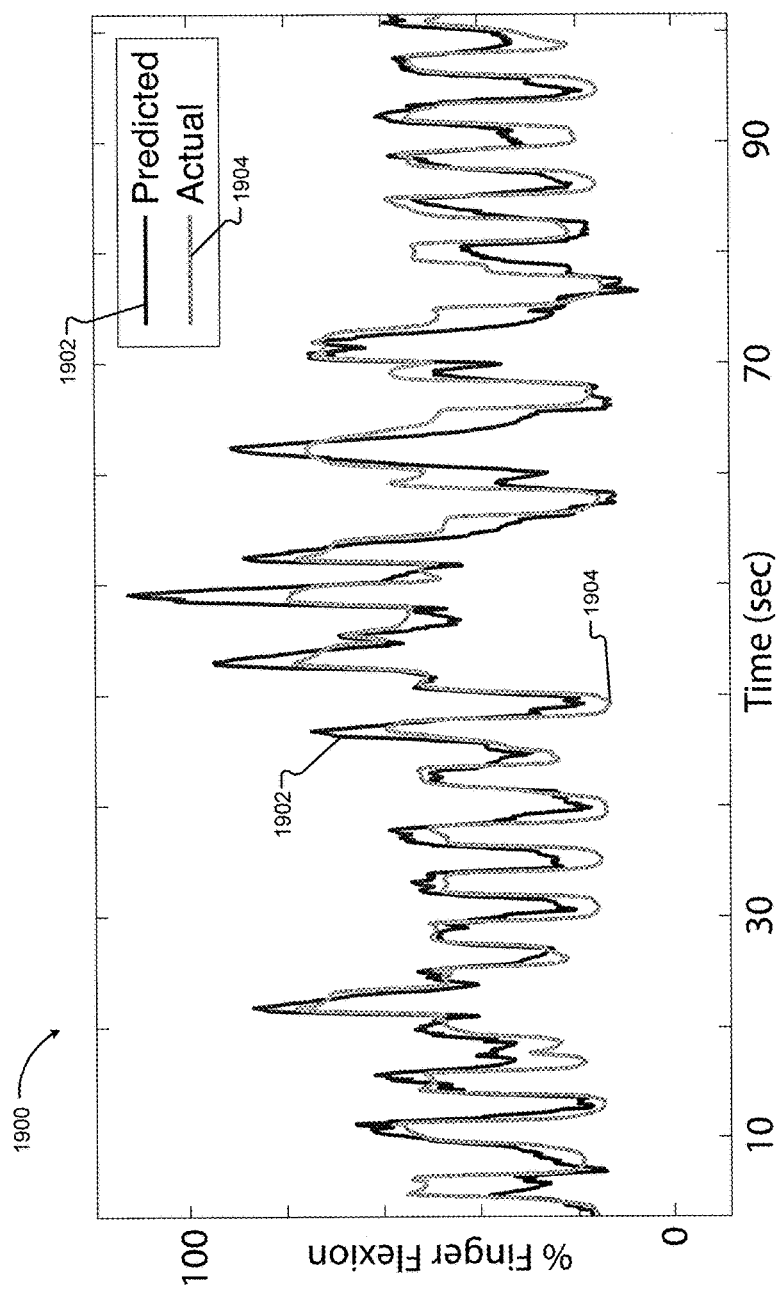

FIG. 19 is a graph of predicted and actual finger flexion percentages over time.

Corresponding reference numerals indicate corresponding parts throughout the several views of the drawings.

It should be noted that the figures set forth herein are intended to exemplify the general characteristics of methods, devices, and materials, among those of the present disclosure, for the purpose of the description of certain embodiments. These figures may not precisely reflect the characteristics of any given embodiment, and are not necessarily intended to fully define or limit specific embodiments within the scope of this disclosure.

DETAILED DESCRIPTION

Example embodiments will now be described more fully with reference to the accompanying drawings. A non-limiting discussion of terms and phrases intended to aid understanding of the present disclosure is provided at the end of this Detailed Description.

In various aspects, the present disclosure provides methods for amplifying and receiving signals from a portion of a nerve, such as individual nerve fascicles, at levels greater than that produced by any conventional methods or techniques. Specifically, as described in further detail below, the present disclosure provides methods for amplifying and receiving signals from a portion of a nerve, like individual nerve fascicles, at greater than or equal to about 150 µV pp and, in some instances, to greater than or equal to about 250 or 500 µV pp and up to, for example, about 1,000 µV pp or more. As mentioned above, signals detected by previous neural interface systems typically were less than 100 µV pp when recording from within the nerve and less than 10 µV pp when recording from a cuff around the nerve. In certain aspects, the present disclosure provides implantable nerve interface devices, also referred to interchangeably as regenerative peripheral nerve interface (RPNI) devices, that facilitate amplification of signals from individual nerve fascicles to greater than or equal to about 150 µV pp and, in some instances, to greater than or equal to about 250 or 500 µV pp and up to, for example, about 1,000 µV pp or more.

Figure 1:
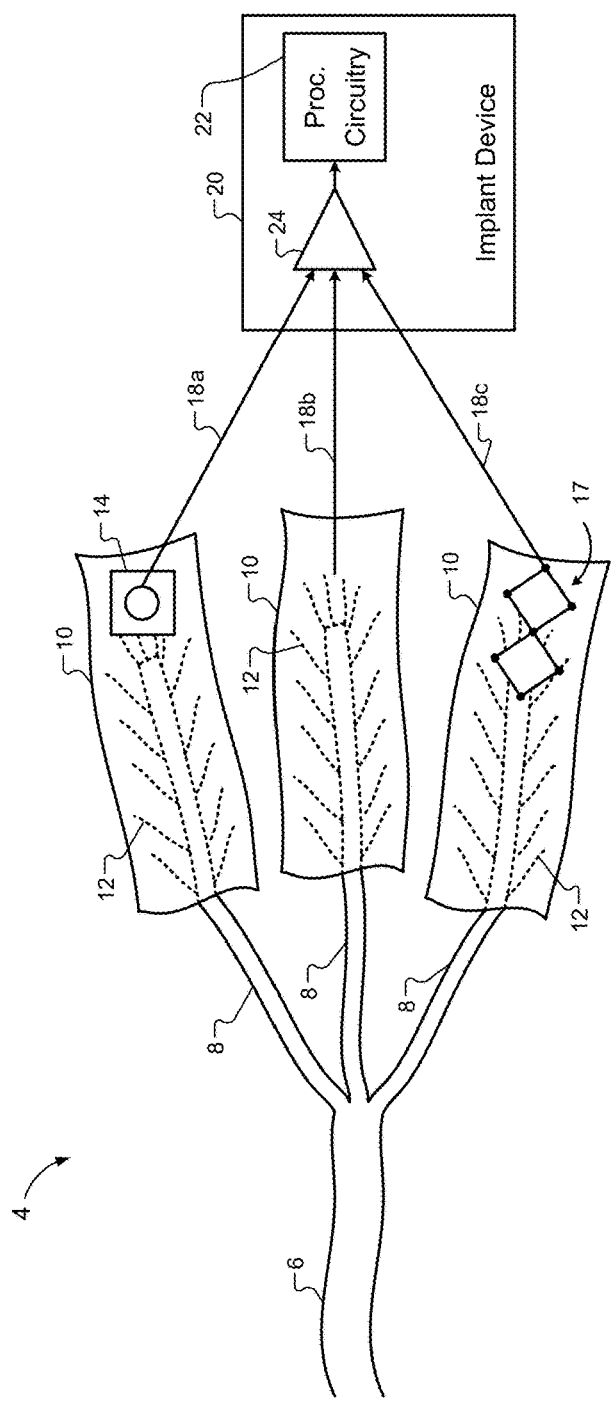
FIG. 1 illustrates a regenerative peripheral nerve interface in accordance with certain aspects of the present disclosure.

With reference to FIG. 1, a neural interface system 4 in a subject or patient is shown. The subject may be an animal with a complex nerve system, such as a mammal, like a human, primate, or companion animal. A portion of a nerve 6, such as a nerve end, of the subject may be damaged or severed, for example, a fully or partially lesioned nerve end caused by injury, disease, or surgery. In certain aspects, the method may include surgically dividing, sectioning, cutting, and/or transecting a portion of a nerve 6 into one or more individual branches or fascicles 8. It should be noted that in certain variations, the method may include isolating a portion of a nerve 6 of interest to create the one or more individual branches or fascicles 8. The one or more individual branches or fascicles 8 are each placed within a free tissue graft 10. In certain aspects, the free tissue graft 10 may be an autograft of muscular tissue or dermis tissue previously harvested from a subject. In certain preferred aspects, the free tissue graft 10 is muscle tissue. The free tissue graft 10 is harvested or resected such that it has a standard, predetermined volume or size depending on the size of the branch or fascicle 8. When harvesting the free tissue graft 10, the tissue graft is devascularized and the native blood vessels no longer function. The predetermined volume of the free tissue graft 10 may be selected to be small enough that it is suitably revascularized by collateral blood flow so that the free tissue graft 10 thrives, while providing a sufficiently sized area or volume for the branches or fascicles 8 of the nerve 6 end to grow, as will be described in greater detail below.

Over a period of, for example, several months, the nerve fascicles 8 can reinnervate the free tissue graft 10 and sprout nerve fibers 12 in search of new neural targets. Once the free tissue graft 10 has been reinnervated, the action potentials from neurons traveling down the nerve then generate muscle level signal amplitudes instead of nerve level amplitudes. In this way, the free tissue grafts 10 (e.g., free muscle grafts) act as an amplifier for the signals generated by the branches or fascicles 8 of nerve 6 end, with the signal from a single nerve fascicle 8 having a voltage amplitude of greater than or equal to about 150 µV pp and, in some instances, greater than or equal to about 250 or 500 µV pp and up to, for example, about 1,000 µV pp or more.

While the neural interface system 4 can be used with any lesioned, sectioned, or damaged portion of a nerve (e.g., nerve ending) within a subject, it is particularly suitable for use with peripheral nerves. The neural interface system 4 may thus be used for peripheral nerves suffering damage or injury, such as those involved with amputations. However, the methods described herein may also be used with a variety of different nerves. Thus, in certain aspects, while the methods of the present disclosure are particularly useful with peripheral nerves, the discussion of peripheral nerves and peripheral nerve interface devices is merely exemplary and non-limiting.

As shown in FIG. 1, the free tissue graft 10 can be configured with an electrical conductor, such as an electrode 14, in electrical communication with the free tissue graft 10. The electrode 14, in turn, is in electrical communication with a wire 18a that is in electrical communication with an implant device 20 including processing circuitry 22 and an amplifier 24, as described in further detail below. In such case, the signal from the nerve fascicle 8 is received by the electrode 14 and communicated over the wire 18a to the processing circuitry 22 of the implant device 20 through, for example, the amplifier 24. Alternatively, the electrode 14 can be omitted and the electrical conductor in electrical communication with the free tissue graft 10 can be a wire 18b placed directly in or on the free tissue graft 10. In such case, the signal from the nerve fascicle 8 is received by the wire 18b itself through direct or indirect electrical communication with the free tissue graft 10 and communicated over the wire 18b to the processing circuitry 22 of the implant device 20 through, for example, the amplifier 24. As a further alternative, the electrical conductor in electrical communication with the free tissue graft 10 can be a wire lattice 17 having a multiplicity of electrode sites and a multiplicity of conducting channels that is placed in or on the free tissue graft 10. The wire lattice 17, in turn, is in electrical communication with a plurality of wires 18c that are in electrical communication with the implant device 20. In such case, the signals from the nerve fascicle 8 are received by the wire lattice 17 and communicated over the wires 18c to the processing circuitry 22 of the implant device 20 through, for example, the amplifier 24. The amplifier 24 is a high impedance amplifier. Further, although a single amplifier 24 is shown in FIG. 1, additional amplifiers, including additional/separate amplifier circuits for one or more individual nerve fascicles 8 or groups of fascicles 8 may also be included in the implant device 20. Additionally, multiple implant devices 20 or implant devices with additional processing circuitry 22 may also be used. As referred to herein, the neural interface system 4 may be implantable nerve interface devices, or RPNI devices, which generally include the free tissue graft 10, the associated wires 18a, 18b, 18c, the electrode 14 or wire lattice 17 with multiple electrodes, if any, and the implant device 20 with the processing circuitry 22.

The implant device 20, for example, may be a medical device implantable within a subject, similar to an automatic cardiac defibrillator, but with processing capabilities to receive, process, record, and/or communicate nerve signals received from the free tissue grafts 10, as described in the present disclosure. Because the signals from the individual nerve fascicles 8 are amplified by the free tissue grafts 10 (e.g., free muscle grafts) to levels greater than or equal to, for example, about 150 μV pp or higher, the electronics contained within the implant device 20 are smaller, cheaper, require less processing power, and/or consume less battery power than the electronics that would be needed to sufficiently and meaningfully receive, record, and process nerve signals detected by previous systems, which, as discussed above, are typically less than 100 μV pp when received from within the nerve and less than 10 μV pp when received from a cuff around the nerve. Further, because the signals from the individual nerve fascicles 8 are amplified by the free tissue grafts 10 to levels greater than or equal to, for example, about 150 μV pp or higher, the signals are less susceptible to noise and interference, have higher signal-to-noise ratios, and more precisely represent and correspond to the actual nerve signals produced by the individual nerve fascicles 8. For example, the signals may have a signal-to-noise ratio of 4 or higher. Notably, electrical signals at such levels may be produced by an implantable neural interface system 4 that in certain aspects, consists essentially of a free tissue graft 10 and one or more electrical conductors (e.g., wires 18a, 18b, 18c, electrode 14, and/or wire lattice 17), along with the one or more portions of the nerve 6 that are regenerated and reinnervated in the free tissue graft.

In certain aspects, a method of amplifying a nerve signal in a subject includes disposing a portion (e.g., nerve fascicles 8) of a nerve 6 within a free tissue graft 10 and securing the portion (nerve fascicles 8) of the nerve 6 therein. For example, the free tissue grafts 10 can be attached to the nerve fascicles 8 via sutures, glue, tension, or other suitable attachment methods or mechanisms. Then, at least electrical conductor (e.g., electrode 14, wires 18a, 18b, 18c, and/or wire lattice 17) may be introduced into the free tissue graft 10. It should be noted that the at least one electrical conductor may be introduced into the free tissue graft prior to securing the portion or branch of the nerve to the free tissue graft. The at least one electrical conductor provides electrical communication with the nerve 6. The electrical conductor may have a maximum thickness of less than or equal to about 5 mm. The one or more portions (nerve fascicles 8) of the nerve 6 thus regenerate within the free tissue graft reinnervating the tissue. Such reinnervation may include growing sprout nerve fibers 12. In this manner, the nerve 6 is thus capable of producing an amplified electrical signal of greater than or equal to about 150 microvolts without any external electrical input, as discussed previously above. Notably, the ability to amplify and generate electrical signals from the nerve reflects a voluntary, spontaneous electrical signal generation from the subject at high voltage levels that were previously not possible. Such a voluntary, spontaneous electrical signal (e.g., generated naturally from motor nerves) can be distinguished from stimulated nerve signals generated by introducing an external electrical input to the nerve for activation (e.g., stimulation by combined compound action potential (CMAPs) resulting from external nerve activation).

In certain other aspects, the method may include cutting a portion of a nerve, such as cutting an ending of the nerve, in the subject to create the one or more branches or fascicles. In certain aspects, the cutting may include cutting the nerve ending into a plurality of portions, like branches/fascicles. Thus, the disposing of the nerve in the free tissue graft and introducing of the electrical conductor into the free tissue graft assembly may be repeated for each respective portion of the nerve. The method may further include harvesting the free tissue graft from a tissue in the subject before the disposing of the cut ending. In certain aspects, the tissue is muscle tissue. In alternative aspects, the tissue may be dermal tissue. As will be discussed in greater detail below, in certain aspects, a maximum dimension of the free tissue graft is less than or equal to about 10 cm. In other aspects, a maximum dimension of the free tissue graft is less than or equal to about 5 cm.

In certain aspects, a method according to certain aspects of the present disclosure may include further stimulating the one or more portions (e.g., branches/fascicles) of the nerve with a stimulus signal delivered through the one or more electrical conductors in electrical communication with the free tissue graft. This provides an ability to deliver sensory feedback via stimulation into the brain of a subject via the neural interface system 4.

Figure 2:
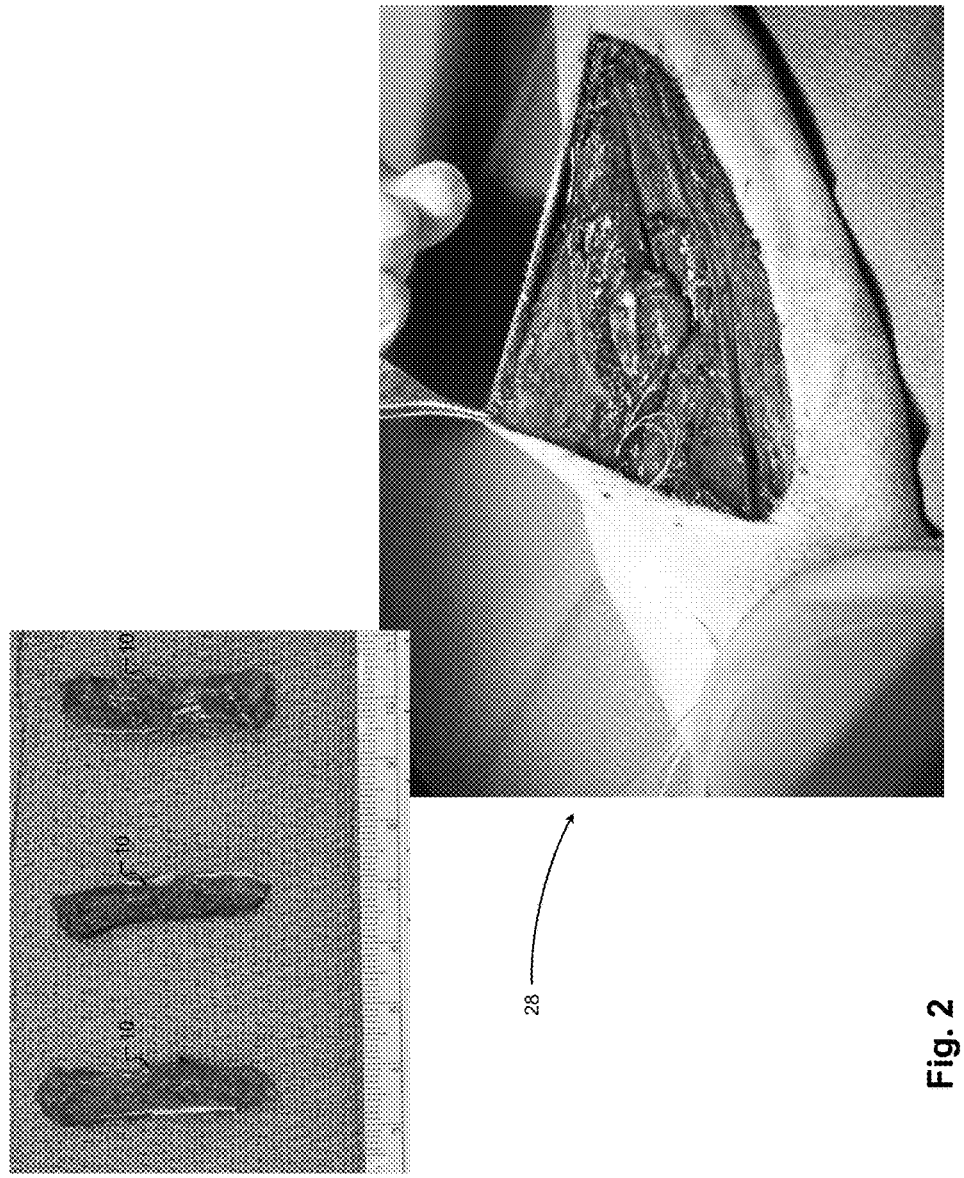
FIG. 2 illustrates three free muscle grafts after being harvested from a subject and a photograph showing a surgical procedure for surgically attaching the free muscle grafts to nerve fascicles of a subject in accordance with certain aspects of the present disclosure.

With reference to FIG. 2, three free tissue grafts 10 of free muscle tissue are shown after being harvested from a subject, but prior to being surgically attached to nerve fascicles of the subject. FIG. 2 further includes a photograph 28 showing a surgical procedure for surgically attaching free tissue grafts 10 to nerve fascicles of a subject. Further description for surgically attaching free tissue grafts 10, such as muscle grafts, also referred to as an autograft of a freely grafted piece of autologous muscle tissue from a subject, to a nerve fascicle is provided at commonly assigned U.S. Pub. 2013/0304174, published on Nov. 14, 2013. The entire disclosure of U.S. Pub. 2013/0304174 is incorporated herein by reference.

Because the free tissue grafts 10, e.g., muscle grafts, may be surgically harvested from non-essential donor muscle within the subject, the free tissue grafts 10 undergo a process of complete deinnervation subsequent to being harvested, whereby previously existing innervation within the free tissue grafts 10 terminates. As discussed above, this harvesting process also causes devascularization of the native cells of the free tissue grafts 10. Once the free tissue grafts 10 are surgically attached to nerve fascicles 8, the free tissue grafts 10 undergo a process of reinnervation, whereby the attached nerve fascicles 8 reinnervate the free tissue grafts 10 and sprout nerve fibers 12, which grow within the free tissue grafts 10 in search of new neural targets. Having previously undergone the process of deinnervation, the signals from the newly attached nerve fascicles 8 and newly sprouted nerve fibers 12 do not have to compete with residual nerve signals from the nerve fascicles and nerve fibers that previously innervated the free tissue grafts 10.

Further, instead of simply dying and being reabsorbed by the subject's body, once surgically reattached to the subject, the free tissue grafts 10 can acquire nutrients through a process of imbibition. As such, even without a native vascular blood supply, if the free tissue graft 10 is within an optimal volume/size range, the free tissue graft 10 can absorb nutrients and blood through the surrounding tissue and fluids to support the process of reinnervation. Eventually, a new blood supply network may be established as the free tissue graft 10 reintegrates with the subject's body. This process of deinnervation of the free tissue graft 10 followed by reinnervation of the free tissue graft 10 by the attached nerve fascicle through newly sprouted nerve fibers 12, coupled with the process of imbibition and revascularization, results in an area of muscle or other tissue from which a highly specific electrical signal from an individual nerve fascicle 8 that is greater than or equal to about 150 μV pp or higher, for example, can be received by, for example, the implant device 20.

As mentioned above, to facilitate the processes of reinnervation and imbibition, the free tissue grafts 10 are preferably within an optimal volume/size range. For example, the volume/size of the free tissue graft 10 may be selected to be small enough that it is quickly revascularized by collateral blood flow, while providing a sufficiently sized area or volume for the nerves to grow without forming disorganized neuromas. A greatest dimension of the free tissue graft 10 may be less than or equal to about 10 cm, in certain preferred aspects. For example, in certain variations, the free tissue graft 10 may have a maximum dimension in any direction of less than or equal to about 10 cm. For example, in certain variations, a length of the free tissue graft 10 may be less than or equal to about 10 cm or, more preferably, less than or equal to about 5 cm. Further, a width of the free tissue graft 10 may be less than or equal to about 10 cm or, more preferably, less than or equal to about 5 cm. The thickness of the free tissue graft 10 may optionally be less than or equal to about 2 to 3 cm. Further, optimal dimensions for the free tissue graft 10 may include a length of less than or equal to about 5 cm and a diameter of greater than or equal to about 2 to less than or equal to about 3 cm. For example, preferred optimal dimensions for the free tissue graft 10 may include a length of approximately 3.5 cm and a diameter of approximately 2 cm. It should be noted that the free tissue graft 10 may have a variety of distinct dimensions and/or geometries and those described herein are exemplary. Additionally, a discussion of the dimensions for freely grafted pieces of autologous muscle tissue from a subject is included at, for example, paragraphs [0082] to [0088] of U.S. Pub. No. 2013/0304174, published Nov. 14, 2013, which is incorporated herein by reference in its entirety.

Figure 3:
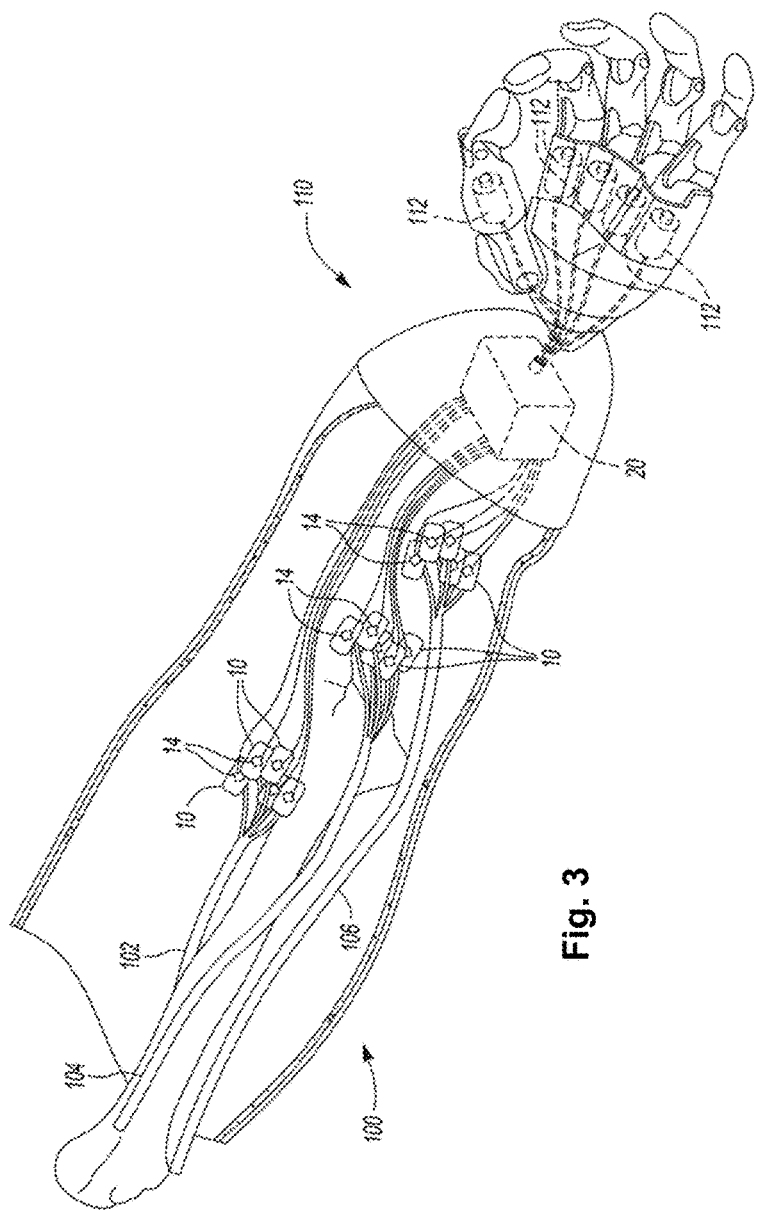
FIG. 3 illustrates another regenerative peripheral nerve interface and a prosthetic device in accordance with certain aspects of the present disclosure.

With reference to FIG. 3, an example embodiment 100 is shown with multiple free tissue grafts 10 (e.g., free muscle grafts) and electrodes 14 connected to an implant device 20. In addition to receiving signals from individual nerve fascicles through free tissue grafts 10 and electrodes 14, the implant device also controls a terminal device, in this case a prosthetic hand 110. Specifically, as shown in FIG. 3, each of the radial nerve 102, the median nerve 104, and the ulnar nerve 106 has been split into multiple individual nerve fascicles that have been attached to corresponding free tissue grafts 10 and are in electrical communication with the processing device 22 of the implant device 20 through electrical communication with electrodes 14.

As discussed in further detail below, the processing circuitry 22 of the implant device 20 monitors the signals from the various fascicles and controls, for example, flexion and extension of the prosthetic hand 110 based on analysis of the received signals. For example, as discussed in further detail below, training data can be obtained through a calibration process whereby the subject is asked to perform certain movements while nerve signals are monitored and recorded by the processing circuitry 22 of the implant device 20 and communicated to an external computing device, such as a desktop computer or laptop. The training dataset is then analyzed and used to estimate parameters used by the processing circuitry 22 to drive the prosthetic hand 110, which are then downloaded from the external computing device to the processing circuitry 22 of the implant device 20. For example, as shown in FIG. 3, the implant device 20 is in communication with actuators 112 that drive flexion and extension of individual fingers of the prosthetic hand 110, as described in further detail below.

Figure 4:
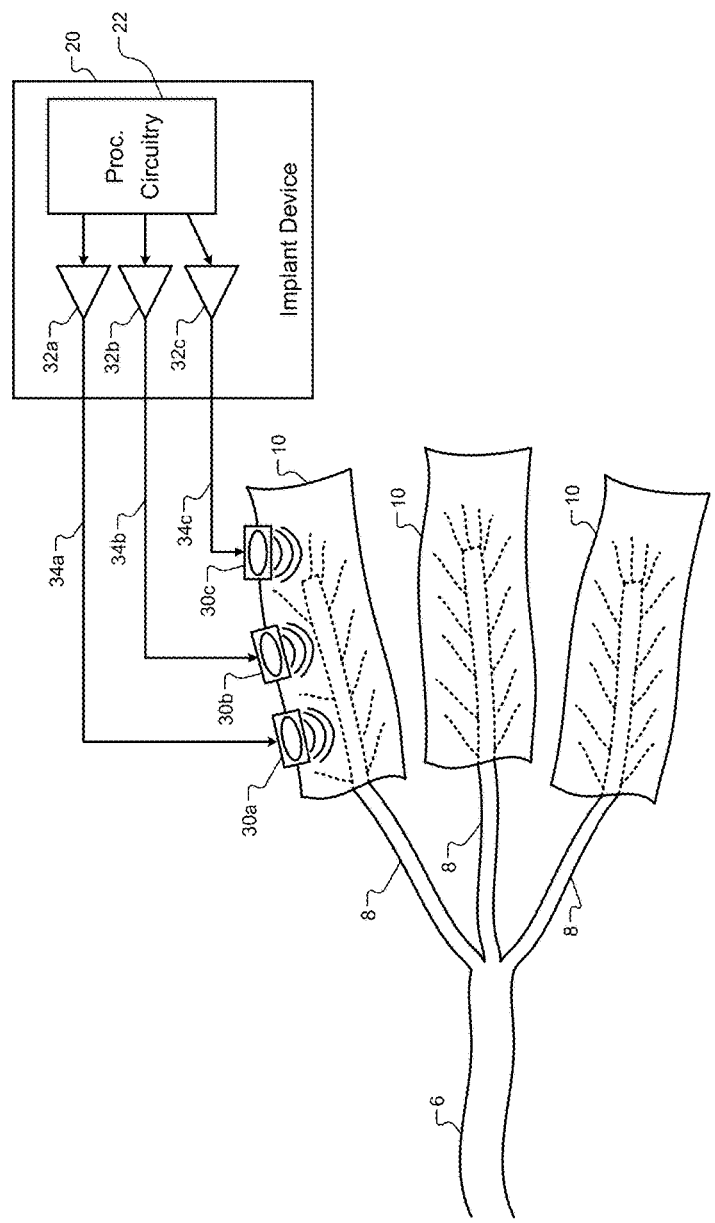
FIG. 4 illustrates another regenerative peripheral nerve interface in accordance with certain aspects of the present disclosure.

With reference to FIG. 4, in addition to sensing or reading signals generated by nerve fascicles 8 amplified through free tissue grafts 10, the RPNI devices of the present disclosure can also be used for stimulating individual nerve fascicles 8 or individual nerve fibers. For example, as shown in FIG. 4, free tissue graft 10 is configured with three electrodes 30a, 30b, 30c in communication with processing circuitry 22 of the implant device 20 through amplifiers 32, 32b, 32c and wires 34a, 34b, 34c. In this way, as discussed in further detail below, processing circuitry 22 can stimulate individual nerve fascicles 8 using, for example, a negative voltage stimulus signal or a positive voltage inhibitory stimulus signal. Generally, negative voltage signals cause nerves to fire while positive voltages inhibit nerves from firing.

Existing clinical applications, such as vagal nerve stimulation, typically use a cuff around an entire nerve. As such, the majority of the nerve is usually stimulated. Using an RPNI device as shown in FIG. 4, however, the processing circuitry 22 can address stimulation to a particular fascicle by directing signals to electrodes 30a, 30b, 30c through wires 34a, 34b, 34c. More specifically, using a free tissue graft 10 can allow for a single fascicle 8, which may be approximately 1 mm in diameter, to be expanded into a 1 cm by 3.5 cm construct for purposes of stimulation. Stimulating the entire construct, i.e., the entire free tissue graft 10, can specifically address the single corresponding fascicle 8.

Further, through the use of multiple electrical contacts, such as multiple electrodes, current steering can be used to enable stimulation of an even more specific area, such as a subsection of a fascicle 8 or individual fibers. For example, when utilizing only a single negative contact for stimulation, the negative voltage may spread and dissipate. By using current steering, on the other hand, the negative voltage can be surrounded by positive voltage to focus the negative voltage on a single location. With continued reference to FIG. 4, a negative voltage may be applied with electrode 30b, while positive voltages may be applied with electrodes 30a and 30c in order to provide greater focus on the location for the application of the negative voltage from electrode 30b.

As discussed in further detail below, nerve stimulation can be used for sensory prostheses to stimulate nerves in response to pressure sensed by pressure sensors of a prosthetic limb, for example. Additionally, nerve stimulation can be used to inhibit pathological pain signals. Additionally, nerve stimulation can be used to inhibit pathological contractions of a bladder for example. Additionally, nerve stimulation can be used for sphincter control, erectile dysfunction, and/or to control nerves associated with visceral organs such as the liver, adrenals, stomach, pancreas, kidneys, and the like. For example, such nerve stimulation may be used on a renal artery to disrupt and treat aberrant nerve signals in the kidneys, which may otherwise cause hypertension.

Figure 5:
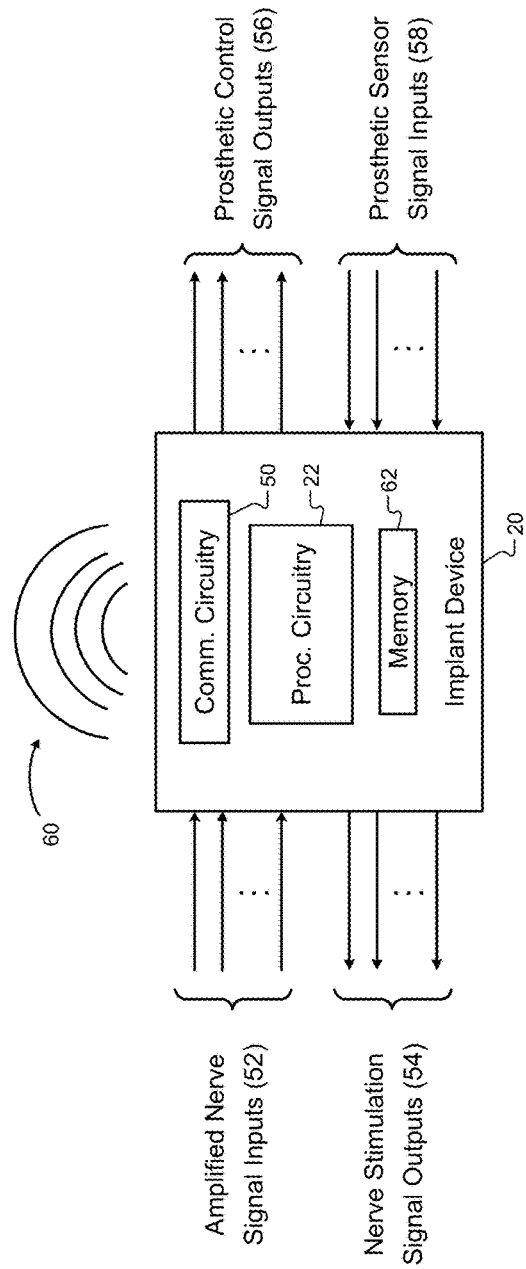
FIG. 5 is a block diagram of an implant device in accordance with certain aspects of the present disclosure.

With reference to FIG. 5, further details are shown for the implant device 20. As discussed above, the implant device 20 can receive amplified nerve signal inputs 52 from the free tissue grafts 10 through wires 18a, 18b, 18c (shown in FIG. 1). As further discussed above, the implant device 20 can communicate nerve stimulation signal outputs 54 to stimulate nerves with electrodes 30a, 30b, 30c, through wires 34a, 34b, 34c (shown in FIG. 4). As further discussed above, the implant device 20 can communicate prosthetic control signal outputs 56 to control movements of a prosthetic device. For example, the implant device 20 can communicate prosthetic control signal outputs 56 to control flexion and extension of the prosthetic hand 110 (shown in FIG. 3) via a data bus, such as a controller area network (CAN) bus. For example, the implant device 20 can communicate the prosthetic control signal outputs 56 to control the individual actuators 112 (shown in FIG. 3) of the prosthetic hand. Further, as further discussed above, implant device 20 can receive prosthetic sensor input signals 58 generated by one or more pressure sensors corresponding to pressure sensed by pressure sensors of a prosthetic limb, for example. As discussed above, implant device 20 can generate nerve stimulation signal outputs 54 based on the pressure sensor signal inputs received by the implant device from the pressure sensors of the prosthetic limb.

As shown in FIG. 5, the implant device includes the processing circuitry 22, as well as communication circuitry 50 and a memory 62, both in communication with the processing circuitry 22. The communication circuitry 50 enables the implant device and, specifically, the processing circuitry 22 of the implant device 20 to wirelessly communicate to computing devices that are external to the implant device 20, including, for example, computing devices that are external to the subject, such as a desktop or laptop computer. In this way, the processing circuitry 22 can communicate data, such as amplified nerve signal input data received via the amplified nerve signal inputs 52. Such communication can be used during a calibration process to receive training and calibration data from the implant device 20 at an external computing device for review and analysis and to communicate estimated operation parameters and configuration data used by the implant device 20 to drive a prosthetic limb, for example, or to generate nerve stimulation signal outputs. The communication circuitry 50 may include an antenna and either a receiver and transmitter or a transceiver for communicating via wireless radio frequency (RF) 60. For example, communication circuitry 50 may communicate via wireless protocols, such as the CEN ISO/IEEE 11073 communication protocol for communication between medical devices and external information system. Alternatively, the communication circuitry 50 may communicate via other wireless protocols, such as WiFi® or Bluetooth®.

The memory 62 can be used by the processing circuitry 22 to store amplified nerve signal input data received via the amplified nerve signal inputs 52 prior to, for example, communication to an external computing device via the communication circuitry 50. The memory 62 can also be used to store estimated operation parameters and configuration data received from an external computing device and used by the implant device during operation. The memory 62 can also be used by the processing circuitry 22 to store event or operation history data, or any other data associated with the various inputs and outputs received or generated by the processing circuitry 22.

Figure 6:
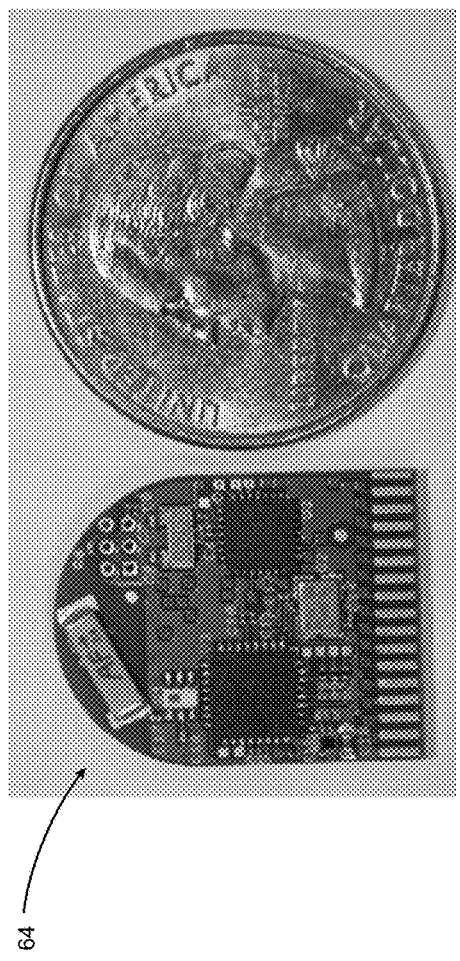
FIG. 6 is a photograph of a hardware device chip in accordance with certain aspects of the present disclosure.

With reference to FIG. 6, a hardware device chip 64 is shown that can include, for example, or be used to implement the processing circuitry 22, communication circuitry 50, and memory 62 of the implant device (shown in FIG. 5). The hardware device chip 64 can also include or be used to implement the amplifier 24 (shown in FIG. 1) and the amplifiers 32a, 32b, 32c (shown in FIG. 4). The hardware device chip 64 can preferably include a high input impedance bioamplifier configured to process the high output impedance biological signals received from the free tissue grafts 10. Further, hardware device chip 64 can preferably include functionality for rejecting large common mode signals, such as recording differentially from paired electrodes, referencing received signals to a local reference near the RPNI device(s), or using a strong high pass filter in a first stage. The hardware device chip 64 can preferably include an amplifier for amplifying the signals received from nerve fascicles 8 by a factor of, for example, 1,000. Preferably, the hardware device chip 64 has very low noise, although this feature may be less important given the relatively high amplitude of the amplified nerve signal inputs received from the nerve fascicles 8. Additionally, the hardware device chip 64 preferably can include a band pass filter to filter received amplified nerve signal inputs between 10,000 to 2,000 Hz before further processing. Additionally, the hardware device chip 64 preferably can take an absolute value in the analog domain of the received amplified nerve signal inputs.

Figure 7:
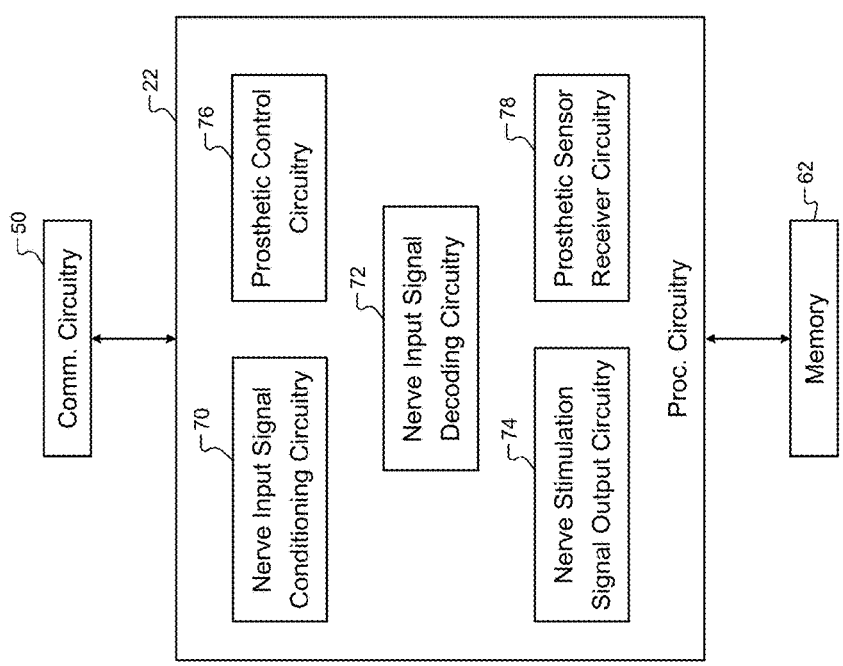
FIG. 7 is a block diagram of processing circuitry with memory and communication circuitry in accordance with certain aspects of the present disclosure.

With reference to FIG. 7, further details are shown for the processing circuitry 22, which is shown in communication with the communication circuitry 50 and the memory 62 of the implant device 20. The processing circuitry 22 includes nerve input signal conditioning circuitry 70 for receiving and conditioning the amplified nerve signal inputs 52 received from nerve fascicles through free tissue grafts 10. The functionality and operation of the nerve input signal conditioning circuitry 70 are discussed in further detail below. The processing circuitry 22 also includes a nerve input signal decoding circuitry 72 for processing and decoding the signal data after conditioning by the nerve input signal conditioning circuitry 70. The functionality and operation of the nerve input signal decoding circuitry 72 are discussed in further detail below. The processing circuitry 22 also includes nerve stimulation signal output circuitry 74 for generating nerve stimulation signal outputs 54. The functionality and operation of the nerve stimulation signal output circuitry 74 are discussed in further detail below. The processing circuitry 22 also includes prosthetic control circuitry 76 for generating prosthetic control signal outputs 56 for controlling a prosthetic limb. The functionality and operation of the prosthetic control circuitry 76 are discussed in further detail below. The prosthetic control signal outputs 56 for controlling the prosthetic limb may be communicated to the prosthetic limb via a data bus, such as a CAN bus. The processing circuitry 22 also includes prosthetic sensor receiver circuitry 78 for receiving prosthetic sensor signal inputs 58 from pressure sensors of a prosthetic limb. The functionality and operation of the prosthetic sensor receiver circuitry 78 are discussed in further detail below.

Figure 8:
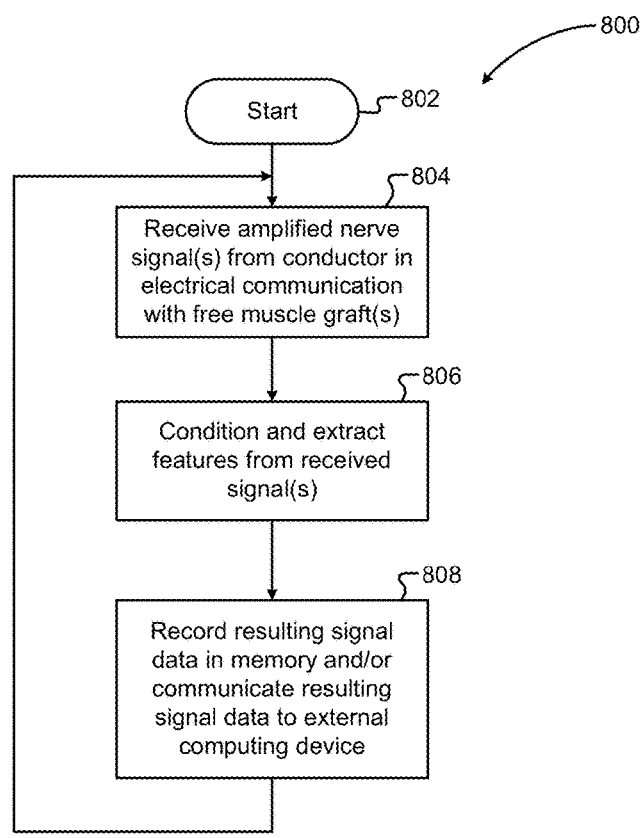
FIG. 8 is a flowchart depicting an example control algorithm for recording amplified nerve signal data in accordance with certain aspects of the present disclosure.

With reference to FIG. 8, a control algorithm 800 is shown for receiving and recording amplified nerve signal data from a free tissue graft 10. The control algorithm 800 may be performed by the processing circuitry 22 of the implant device 20. More specifically, the control algorithm 800 may be performed, at least in part, by the nerve input signal conditioning circuitry 70 (shown in FIG. 7) of the processing circuitry 22. The control algorithm 800 starts at 802.

At 804, the nerve input signal conditioning circuitry 70 of the processing circuitry 22 receives the amplified nerve signal(s) from the conductor in electrical communication with the free muscle graft(s). As described in detail above with reference to FIG. 1, the electrical conductor may be an electrode 14, a wire lattice 17, or a wire 18b in electrical communication with the free tissue graft 10. As further described above, the electrical signal can have a voltage amplitude of greater than or equal to about 150 μV pp and, in some instances, greater than or equal to about 250 or 500 μV pp and up to, for example, about 1,000 μV pp or more. Further, in embodiments where an amplifier 24 (shown in FIG. 1) is used, the signals may be amplified prior to being received by the processing circuitry 22. In such case, for example, the signals may be pre-conditioned by being amplified by a factor of 1,000 with amplifier 24 prior to being received by the nerve input signal conditioning circuitry 70 of the processing circuitry 22.

At 806, the nerve input signal conditioning circuitry 70 of the processing circuitry 22 conditions and extracts features from the received signal from the free tissue graft 10. For example, in embodiments that do not include an amplifier 24 (shown in FIG. 1), the nerve input signal conditioning circuitry 70 may amplify the received signals by, for example, a factor of 1,000. The nerve input signal conditioning circuitry 70 may then filter the received signal using a predetermined analog frequency range. For example, the predetermined analog frequency range may be between 10 and 1,000 Hz or between 10 and 2,000 Hz. After filtering, the nerve input signal conditioning circuitry 70 may digitize the filtered signal using a predetermined sampling rate. For example, the nerve input signal conditioning circuitry 70 may digitize the filtered signal using a sampling rage of 30,000 samples per second. The digitized signal may then be digitally filtered using a predetermined digital frequency range. For example, the predetermined digital frequency range may be 100 to 500 Hz. After digital filtering, the signal may then be down-sampled to 1,000 samples per second. Because of the relatively large voltage amplitude of the initially received signal, the conditioning and feature extraction performed at step 806 results in a robust and well-defined signal that is less susceptible to noise or interference, as compared with systems that do not utilize free tissue grafts 10 for amplification of signals from nerve fascicles.

At 808, the processing circuitry 22 records the resulting signal data in memory 62 and/or communicates the resulting signal data to an external computing device using the communication circuitry 50. For example, the resulting signal data can be stored in the memory 62 of the implant device 20 and then communicated via a batch communication process to an external computing device through the communication circuitry 50. Alternatively, the memory 62 can serve as a buffer that receives and stores the resulting signal data for further processing by the processing circuitry 22 or communication to an external computing device through the communication circuitry 50. Alternatively, the resulting signal data can be streamed to an external computing device in real-time through the communication circuitry 50.

After recording or communicating the resulting signal data at 808, the processing circuitry 22 loops back to 804 and continues to receive amplified nerve signal(s). Although the control algorithm 800 is shown as sequential steps for purposes of illustration, it is understood that the individual steps can occur continually in parallel by the processing circuitry 22 as amplified nerve signals are continually received in real-time.

Figure 9:
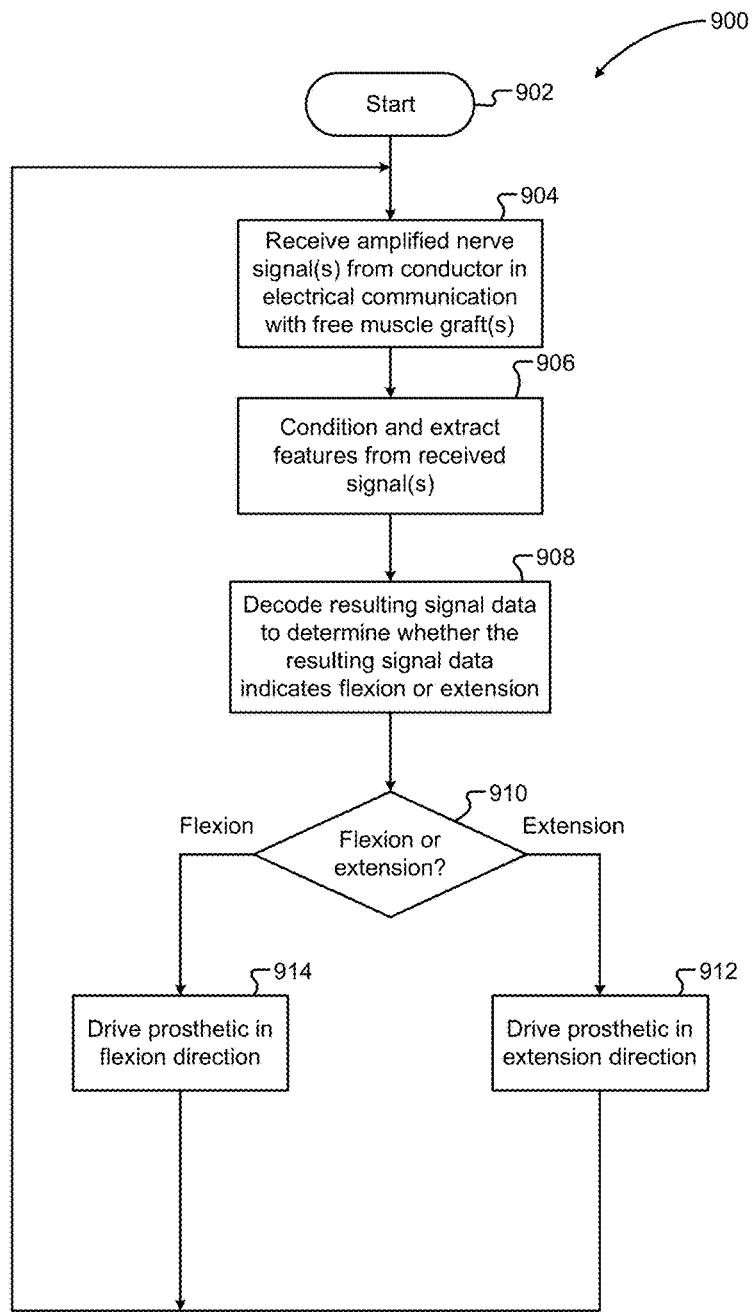
FIG. 9 is a flowchart depicting an example control algorithm for control of a prosthetic limb in accordance with certain aspects of the present disclosure.

With reference to FIG. 9, a control algorithm 900 is shown for controlling a prosthetic limb, such as a prosthetic hand 110 (shown in FIG. 3) based on signals received from the from the free tissue grafts 10. The control algorithm 900 may be performed by the processing circuitry 22 of the implant device 20. More specifically, the control algorithm 900 may be performed, at least in part, by the nerve input signal conditioning circuitry 70, the nerve input signal decoding circuitry 72, and the prosthetic control circuitry 76 (shown in FIG. 7) of the processing circuitry 22. The control algorithm 900 starts at 902.

At 904, the nerve input signal conditioning circuitry 70 of the processing circuitry 22 receives the amplified nerve signal(s) from the conductor in electrical communication with the free muscle graft(s). The functionality of step 904 is described above with respect to step 804 of FIG. 8 and is not repeated here.

At 906, the nerve input signal conditioning circuitry 70 of the processing circuitry 22 conditions and extracts features from the received signal from the free tissue graft 10. The functionality of step 906 is described above with respect to step 806 of FIG. 8 and is not repeated here.

At 908, the nerve input signal decoding circuitry 72 decodes the resulting signal data to determine whether the resulting signal data corresponds to, for example, flexion or extension of the prosthetic limb. While the control algorithm 900 of FIG. 9 is described in terms of decoding the resulting signal data for flexion or extension actions, it is understood that other prosthetic limb control movements could likewise be decoded from the resulting signal data, as appropriate. The nerve input signal decoding circuitry 72 may use a one of two classifier, such as a Naïve Bayes classifier, or regression analysis, to determine whether the resulting signal data over a predetermined time period segment, such as 25 milliseconds (ms), indicates either flexion or extension. Further details for decoding the resulting signal data are described below with respect to the control algorithm 1000 for decoding signals for control of a prosthetic limb shown in FIG. 10.

At 910, the processing circuitry 22 determines whether the resulting signal data for the predetermined time period segment corresponds to either flexion or extension of the prosthetic limb. At 910, when the resulting signal data corresponds to extension, the processing circuitry proceeds to 912 and the prosthetic control circuitry 76 of the processing circuitry 22 drives the prosthetic limb in the extension direction. At 910, when the resulting signal data corresponds to extension, the processing circuitry proceeds to 914 and the prosthetic control circuitry 76 of the processing circuitry 22 drives the prosthetic limb in the flexion direction. For example, in the case of a prosthetic hand 110, as shown in FIG. 3, the processing circuitry 22 can drive actuators 112 of the prosthetic hand 110 in either a flexion or extension direction, as appropriate. After driving the prosthetic limb at steps 912 or 914, the processing circuitry 22 loops back to 904.

Figure 10:
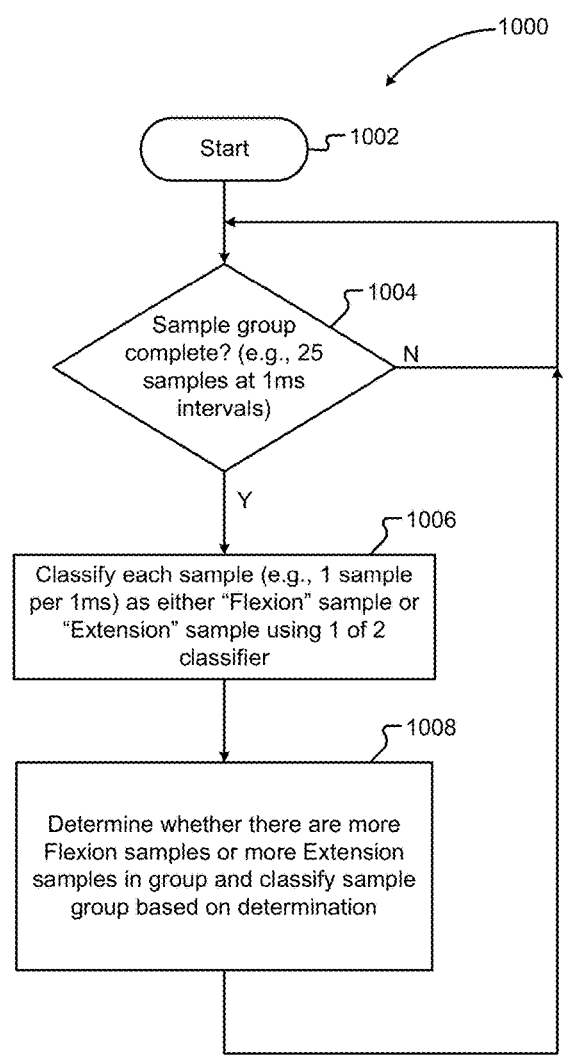
FIG. 10 is a flowchart depicting an example control algorithm for decoding signal for control of a prosthetic limb in accordance with certain aspects of the present disclosure.

With reference to FIG. 10, a control algorithm 1000 is shown for decoding signals for control of a prosthetic limb. The control algorithm 1000 may be performed by the processing circuitry 22 of the implant device 20. More specifically, the control algorithm 1000 may be performed, at least in part, by the nerve input signal decoding circuitry 72. The functionality of control algorithm 1000 shown in FIG. 10 is encapsulated in step 908 of FIG. 9. The control algorithm 1000 starts at 1002.

At 1004, the nerve input signal decoding circuitry 72 determines whether a current sample group for a predetermined time period segment is complete. For example, the predetermined time period segment may be 25 ms and the sample interval may be a 1 ms interval. In such case, the nerve input signal decoding circuitry 72 may wait at step 1004 until a complete sample group of 25 samples at 1 ms intervals is complete. When it is not yet complete, the nerve input signal decoding circuitry 72 loops back to 1004. When it is complete, the nerve input signal decoding circuitry 72 proceeds to 1006.

At 1006, the nerve input signal decoding circuitry 72 classifies each sample in the sample group using a one-of-two classifier. For example, when the nerve input signal decoding circuitry 72 is decoding the resulting signal data for either flexion or extension, the nerve input signal decoding circuitry 72 may classify each sample within the sample group as either a flexion sample or an extension sample. For example, the nerve input signal decoding circuitry 72 may use a one-of-two Naïve Bayes classifier, or regression analysis, to classify each sample within the sample group as either a flexion sample or an extension sample.

The one-of-two Naïve Bayes classifier can use training data collected earlier from the subject during calibration procedures and routines. For example, the subject may be commanded to perform a flexion or an extension action and the resulting nerve signal data can be recorded by the processing circuitry 22 and communicated to an external computing device for analysis. Based on the collected training data, Gaussian distributions can be estimated or computed, based on the received nerve signal data, for each of the flexion and extension movements. For example, the Gaussian distributions for the flexion and extension movements will then have different means and variances. The parameters and data for the one-of-two Naïve Bayes classifier can be estimated based on the collected training data by an external computing device and then communicated to the processing circuitry 22 and stored in memory 62 for use by the nerve input signal decoding circuitry 72 in decoding nerve signal data.

During step 1006, the nerve input signal decoding circuitry 72 can compare each sample within the sample group to the previously determined Gaussian distributions having different means and variances for flexion and extension movements and calculate a probability that the particular sample was drawn from each of the two distributions. Each sample is then classified based on which of the two movements has a higher probability for the particular sample. For example, if a particular sample has a higher probability that it corresponds to a flexion movement, the sample is classified as a flexion sample. If the particular sample has a higher probability of corresponding to an extension movement, the sample is classified as an extension sample. Once all of the samples within the sample group have been classified, the nerve input signal decoding circuitry 72 proceeds to 1008.

At 1008, the nerve input signal decoding circuitry 72 determines whether there are more flexion samples or more extension samples in the particular sample group and classifies the entire sample group based on the determination. For example, when there are more flexion samples in the sample group, the sample group is classified as a flexion sample group and when there are more extension samples in the sample group, the sample group is classified as an extension sample group. In this way, the nerve input signal decoding circuitry 72 predicts whether a group of samples in the particular sample group is indicating a flexion movement or an extension movement, for example. It is understood that other movements may likewise be included in the classification and prediction process. After classifying the sample group, the nerve input signal decoding circuitry 72 loops back to 1004.

In this way, with reference to both FIGS. 9 and 10, the processing circuitry 22 can determine or predict, for example, whether the nerve signal data for a particular predetermined time period segment, such as 25 ms, corresponds to or is indicating a flexion movement or an extension movement. Further, the prosthetic control circuitry 76 can send control commands to the prosthetic limb every 25 ms based on the classification of the current or most recent sample group. In this way, the processing circuitry 22 can continually monitor and decode the nerve signal data and send corresponding commands to operate the prosthetic limb. While the above examples are described using a predetermined time period segment, it is understood that shorter or longer predetermined time period segments can be used.

Figure 11:
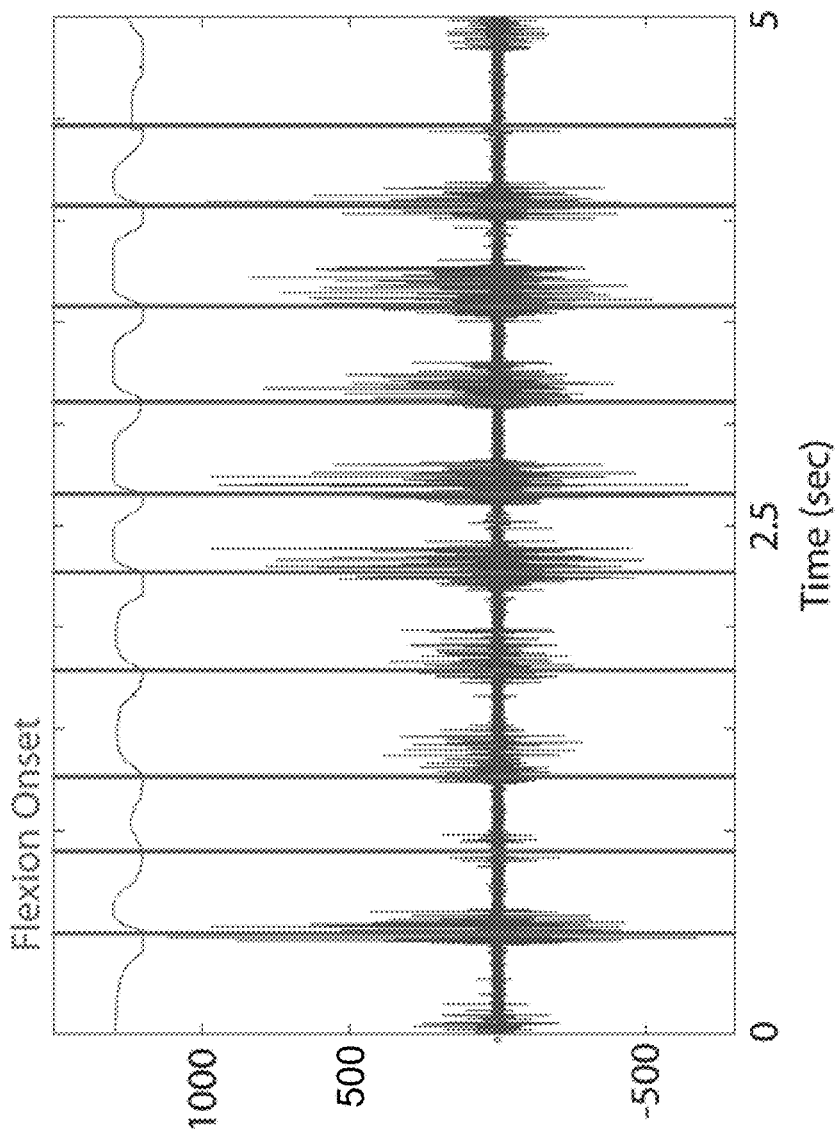
FIG. 11 is a graph showing nerve signal data corresponding to onset of a flexion movement.

With reference to FIG. 11, an example graph is shown with nerve signal data over a 5 second time period corresponding to onset of a flexion movement. Similarly, with reference to FIG. 15, an example graph is shown with nerve signal data over a 400 millisecond time period corresponding to onset of a finger flexion movement.

As described above with respect to FIGS. 9 and 10, training data collected from the subject during a calibration routine can be used to generate a mapping, for example, of received nerve signals to corresponding prosthetic limb movements or actions. In an example of a transradial amputee, individual nerve fascicles may map well to individual hand muscles simulated with the prosthetic limb. In an example of a transhumeral amputee, the training data can be used to determine which nerve fascicles or sets of nerve signal inputs correlate best to which individual hand muscles simulated with the prosthetic limb.

Additionally, nerve signal data, such as average signal power, number of zero crossing events, or count of detected spikes can also be monitored, recorded, and analyzed for each signal from each nerve fascicles and used to calculate a desired velocity, for example, for all five fingers of a prosthetic hand to send in a single command to the prosthetic hand at each time step, e.g., each 25 ms. There is not a one-to-one correspondence between particular muscles and the velocity of individual fingers. For example, to flex only a pinkie finger, a subject may need to simultaneously extend an index finger. As such, finger velocities can be regressed against muscle activity across all of the nerve signal channels to determine a consistent overall map. Various algorithms are available to estimate instantaneous velocities from a variety of signals, including, for example, linear filters, Kalman filters, and particle filters.

Additionally, individual discrete states, like grasping and pointing, can be predicted using linear discriminants, Naïve Bayes classifiers, or support vector machines. In each case, a training dataset is obtained through a calibration process by asking the subject to perform a variety of movements or actions and monitoring and recording the resulting nerve signal data using the implant device 20 and processing circuitry 22. The training dataset can then be used to estimate operational parameters used by the processing circuitry 22 and, for example, the prosthetic control circuitry 76, to control the prosthetic hand. The estimated operation parameters can then be downloaded to the processing circuitry 22 through the communication circuitry 50 and stored in memory 62 for use by the processing circuitry 22 to make real-time estimations of finger velocity to drive the prosthetic hand, for example.

Figure 12:
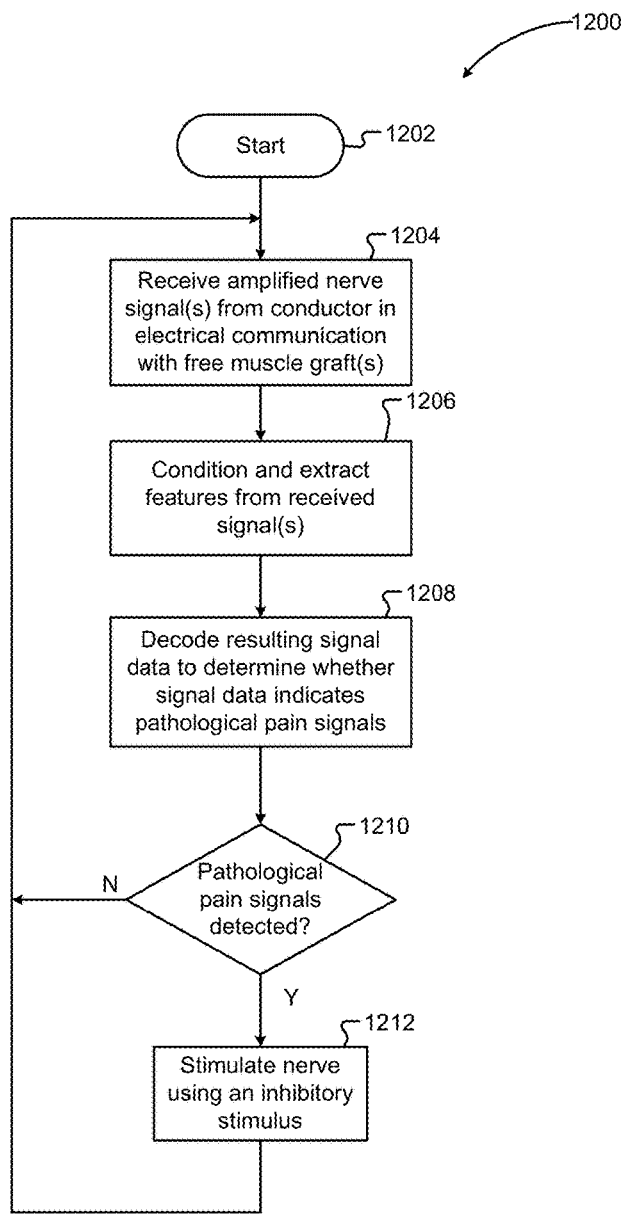
FIG. 12 is a flowchart depicting an example control algorithm for monitoring nerves for pathological pain signals in accordance with certain aspects of the present disclosure.

With reference to FIG. 12, a control algorithm 1200 is shown for monitoring nerves for pathological pain signals. The control algorithm 1200 may be performed by the processing circuitry 22 of the implant device. More specifically, the control algorithm 1200 may be performed, at least in part, by the nerve input signal conditioning circuitry 70, the nerve input signal decoding circuitry 72, and the nerve stimulation signal output circuitry 74. The control algorithm 1200 starts at 1202.

At 1204, the nerve input signal conditioning circuitry 70 of the processing circuitry 22 receives the amplified nerve signal(s) from the conductor in electrical communication with the free muscle graft(s). The functionality of step 1204 is described above with respect to step 804 of FIG. 8 and is not repeated here.

At 1206, the nerve input signal conditioning circuitry 70 of the processing circuitry 22 conditions and extracts features from the received signal from the free tissue graft 10. The functionality of step 1206 is described above with respect to step 806 of FIG. 8 and is not repeated here.

At 1208, the nerve input signal decoding circuitry 72 decodes the resulting signal data to determine whether the resulting signal data indicates, for example, pathological pain signals. The decoding performed at 1208 is similar to the decoding described above with respect to step 908 of FIG. 9 and steps 1004 to 1008 of FIG. 10, which describe decoding resulting signal data to determine whether the resulting signal data indicates flexion or extension actions. Like the decoding described above with respect to FIGS. 9 and 10, the decoding performed at 1208 can likewise use a one of two classifier, such as a Naïve Bayes classifier, based on a training data set collected during a calibration procedure with the subject, to determine whether the resulting signal data corresponds to a state where pathological pain signals are being generated or not. After decoding the resulting signal at 1208, the processing circuitry 22 proceeds to 1210.

At 1210, the processing circuitry 22 determines whether pathological pain signals have been detected based on the decoding of the resulting signal data. When pathological pain signals are detected, the processing circuitry 22 proceeds to 1212 and stimulates the appropriate nerve fascicles with an inhibitory stimulus. Specifically, the nerve stimulation signal output circuitry 74 of the processing circuitry 22 can stimulate the appropriate nerve fascicle with a positive voltage to inhibit neural activity and inhibit or reduce the pathological pain signal activity in the nerve fascicle. In this way, pain signals within the subject can be mitigated without permanently losing sensation in the particular nerves or nerve fascicles at issue. At 1212, after stimulating the nerve using an inhibitor stimulus, or at 1210 after determining that pathological pain signals have not been detected, the processing circuitry 22 loops back to 1204.

Figure 13:
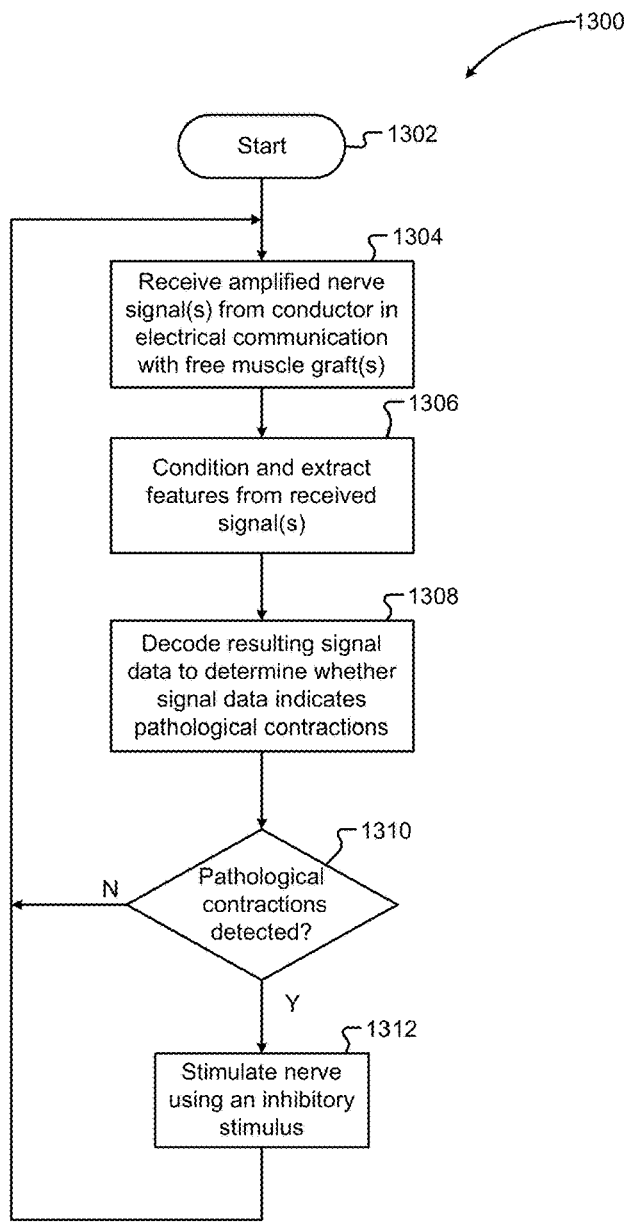
FIG. 13 is a flowchart depicting an example control algorithm for monitoring pathological bladder contraction signals in accordance with certain aspects of the present disclosure.

With reference to FIG. 13, a control algorithm 1300 is shown for monitoring pathological bladder contraction signals. The control algorithm 1300 may be performed by the processing circuitry 22 of the implant device. More specifically, the control algorithm 1300 may be performed, at least in part, by the nerve input signal conditioning circuitry 70, the nerve input signal decoding circuitry 72, and the nerve stimulation signal output circuitry 74. The control algorithm 1300 starts at 1302.

At 1304, the nerve input signal conditioning circuitry 70 of the processing circuitry 22 receives the amplified nerve signal(s) from the conductor in electrical communication with the free muscle graft(s). The functionality of step 1304 is described above with respect to step 804 of FIG. 8 and is not repeated here.

At 1306, the nerve input signal conditioning circuitry 70 of the processing circuitry 22 conditions and extracts features from the received signal from the free tissue graft 10. The functionality of step 1306 is described above with respect to step 806 of FIG. 8 and is not repeated here.

At 1308, the nerve input signal decoding circuitry 72 decodes the resulting signal data to determine whether the resulting signal data indicates, for example, pathological bladder contraction signals. The decoding performed at 1308 is similar to the decoding described above with respect to step 908 of FIG. 9 and steps 1004 to 1008 of FIG. 10, which describe decoding resulting signal data to determine whether the resulting signal data indicates flexion or extension actions. Like the decoding described above with respect to FIGS. 9 and 10, the decoding performed at 1308 can likewise use a one of two classifier, such as a Naïve Bayes classifier, based on a training data set collected during a calibration procedure with the subject, to determine whether the resulting signal data corresponds to a state where pathological bladder contraction signals are being generated or not. After decoding the resulting signal at 1308, the processing circuitry 22 proceeds to 1310.

At 1310, the processing circuitry 22 determines whether pathological bladder contraction signals have been detected based on the decoding of the resulting signal data. When pathological bladder contraction signals are detected, the processing circuitry 22 proceeds to 1312 and stimulates the appropriate nerve fascicles with an inhibitory stimulus. Specifically, the nerve stimulation signal output circuitry 74 of the processing circuitry 22 can stimulate the appropriate nerve fascicle with a positive voltage to inhibit neural activity and inhibit or reduce the pathological bladder contraction signal activity in the nerve fascicle. At 1312, after stimulating the nerve using an inhibitor stimulus, or at 1310 after determining that pathological pain signals have not been detected, the processing circuitry 22 loops back to 1304.

Although described in the context of monitoring and inhibiting pathological bladder contraction signals, the control algorithm 1300 described with respect to FIG. 13 can likewise be adapted for other applications. For example, the control algorithm 1300 could be appropriately adapted for sphincter control or erectile dysfunction. Likewise, the control algorithm 1300 could, for example, be adapted to control nerves associated with visceral organs such as the liver, adrenals, stomach, pancreas, and kidneys. In each case, training data is collected and analyzed from the subject to generate appropriate monitoring parameters, which are then downloaded to the implant device 20. The implant device 20 then monitors nerve signal activity to determine whether nerve stimulation is appropriate.

With reference to FIG. 14, a control algorithm 1400 is shown for stimulating nerves based on sensed pressure signals from a prosthetic device. For example, a prosthetic device, such as the prosthetic hand 110 shown in FIG. 3, may be equipped with pressure sensors located, for example, in the fingertips of the prosthetic. The pressure sensors may sense pressure and communicate pressure signals back to the processing circuitry 22 of the implant device 20. The control algorithm 1400 may be performed by the processing circuitry 22 of the implant device. More specifically, the control algorithm 1400 may be performed, at least in part, by the prosthetic sensor receiver circuitry 78 and the nerve stimulation signal output circuitry 74. The control algorithm 1400 starts at 1402.

At 1404, the prosthetic sensor receiver circuitry 78 receives the pressure signals from the pressure sensors of the prosthetic, corresponding to sensed pressure at the location of the pressure sensors. At 1406, the nerve stimulation signal output circuitry 74 stimulates individual nerve fascicles based on the received sensed pressure signals. A calibration procedure with the subject can be used to generate training data to determine which individual nerve fascicles should most appropriately be mapped to which pressure sensors. Further, the firing rate or level of the stimulation can correspond to the level of pressure sensed by the pressure sensors. In this way, the implant device can communicate tactile feedback signals from the prosthetic to the appropriate nerve fascicles.

The following specific examples are provided for illustrative purposes of how to make and use the compositions, devices, and methods of this technology and, unless explicitly stated otherwise, are not intended to be a representation that given embodiments of this technology have, or have not, been made or tested.

EXAMPLES

Example 1

RPNI Studies in Non-Human Primates

In the following example, RPNIs were surgically implanted in the forearms of two nonhuman primates: Monkey R and Monkey L. Specifically, Monkey R had three RPNIs implanted and Monkey L had four RPNIs implanted. Muscle grafts were attached to small branches of the median and radial nerves, providing independent finger flexion/extension and thumb flexion signals. The surgery followed a standard operating procedure checklist and the animals were monitored in-cage daily for ten days post-op and then observed in a primate chair during daily experiments thereafter.

No major complications were noted and the animals regained normal use of the limb within one week after surgery. In a second surgery in both animals, muscle grafts were observed with obvious revascularization. In response to electrical stimulation, the RPNIs produced large amplitude compound muscle action potentials (CMAPs), indicating reinnervation of the muscle grafts by the implanted nerve fascicles.

In a third surgery in Monkey L, four bipolar "IM-MES" intramuscular electrodes manufactured by Ardiem Medical were implanted in the two mature RPNIs and in a healthy, intact muscle (the ECRB, a wrist extensor) for comparison. One electrode was placed in the muscle graft of a newly-created RPNI construct, which subsequently matured over three months to produce high amplitude signals. The presence of the electrode during the maturation phase did not negatively impact the regeneration, reinnervation, and maturation of the RPNI. The electrode leads were tunneled subcutaneously from the monkey's forearm to the back, where they exited percutaneously for connection to recording equipment. Daily recordings from these implanted electrodes were taken during task behavior. The percutaneous site with the exiting leads was lightly cleaned with a betadine solution weekly and no infection was noted. The site appeared clean, with minimal irritation, and did not cause any obvious discomfort for the animal.

With reference to FIG. 16, graph 1600 shows voluntary RPNI signals, in μV, recorded by semi-chronic Ardiem IM-MES electrodes in Monkey L, along with the calculated flexed percentage corresponding to the RPNI signals. Graph 1602 shows voluntary RPNI signals, in μV, recorded by percutaneous fine-wire electrodes in Monkey L along with the calculated flexed percentage corresponding to the RPNI signals. Graph 1604 shows voluntary RPNI signals, in μV, recorded by percutaneous fine-wire electrodes in Monkey R along with the calculated flexed percentage corresponding to the RPNI signals.

With reference to graph 1600, signals recorded by the IM-MES electrodes vary between animals and RPNI grafts with amplitudes ranging from 50-500 μV pp. The graphs 1600, 1602, 1604 show representative signals, which look similar to sparse electromyographic (EMG) signals, usually displaying multiple apparent single motor units. The rightmost portion of graph 1600 shows a zoomed in portion of the voltage signal showing individual muscle twitches. All putative single units observed correspond reliably to flexion events, are about four ms in length, and have a variable firing frequency. The high signal to noise ratio (SNR) of the RPNI signal allowed an automated detection of voluntary RPNI activation with 95+% accuracy, using a linear discriminant classifier. The RPNI signals were used to control a prosthetic hand in real-time, while Monkey L was performing the behavioral task.

Example 2

RPNI Studies in Humans

In the following example, three RPNIs were surgically implanted in a human for the purpose of neuroma control. The patient had a distal transradial amputation just proximal to the wrist. Muscle grafts of approximately 1×3 cm were taken from surrounding tissue and sutured separately onto the distal ends of the median, ulnar, and radial nerves. At this level, the radial nerve (and thus the RPNI graft) contains only sensory fibers which originally innervated the dorsal skin of the hand. The median and ulnar nerves and RPNIs contain a mix of sensory fibers to the hand and motor fibers which originally innervated the intrinsic muscles of the hand. Electromyographic (EMG) activity was recorded from the median and ulnar RPNIs using percutaneous fine-wire electrodes while the patient performed several hand movements. As expected, RPNIs produced EMG in response to movements which engaged muscles originally innervated by the amputated nerves.

With reference to FIG. 17, graphs 1700 and 1702 show signals recorded from the median-nerve RPNI, the ulnar-nerve RPNI, and a healthy wrist muscle (the Flexor Carpi Ulnaris-FCU) during two different hand movements. Specifically, graph 1700 shows signals recorded during a thumb-little opposition action, which corresponds to touching the tip of the thumb to the tip of the little finger. Graph 1702 shows signals recorded during a thumb opposition action, which corresponds to touching the tip of the thumb to the base of the little finger, without flexing the little finger. These graphs illustrate that physiologically-correct signals were obtained from the RPNIs. In other words, the nerves are activated during the correct movements.

As expected, the median RPNI signals (shown in the top row of graphs 1700 and 1702) display similar activity amplitudes during both thumb-little opposition and thumb-only opposition. This is because the median nerve originally innervated thumb muscles, but not little finger muscles. The ulnar RPNI signals (shown in the bottom row of graphs 1700 and 1702) are more activated during thumb-little opposition than thumb-only opposition, as the ulnar nerve originally innervated more muscles devoted to the little finger than to the thumb. Finally, the healthy FCU muscle activity, though clearly present, is not correlated to either movement, as it is devoted entirely to flexion of the wrist.

Taken together, graphs 1700 and 1702 show that the RPNIs are being innervated by the expected nerves, as there should be no way to achieve the same pattern of activity via the healthy, intact muscles surrounding the RPNIs.

With reference to FIG. 18, graph 1800 shows signals recorded from the ulnar RPNI during a key pinch movement, which corresponds to making a first with the thumb held against the lateral aspect of the index finger, i.e., the shape made when turning a key in a car ignition. Graph 1800 illustrates the high signal amplitude achievable through the RPNI technique. For example, the signal-to-noise ratio (SNR) of the data in graph 1800 is 8.65.

Example 3

Continuous Position Control Studies in Non-human Primates

In the following example, nerve signals in a monkey were sensed and monitored while the monkey flexed and extended a finger. The nerve signals were processed using the techniques described above with respect to the present teachings, including the use of a Kalman filter, and a percentage of flexion was predicted based on the nerve signals. In addition, the actual percentage of flexion of the monkey's finger was monitored and compared to the predicted percentage of flexion.

With reference to FIG. 19, graph 1900 shows the predicted percentage of flexion 1902 graphed over time along with the actually observed percentage of flexion in the finger. In graph 1900, the predicted percentage of flexion 1902 correlates to the actual percentage of flexion 1904 by a correlation factor of 0.87. Graph 1900 illustrates the accuracy of the techniques described above with respect to the present teachings, including the use of a Kalman filter, when predicting the actual percentage of flexion based on the monitored nerve signals. In this way, the techniques of the present teachings can be used for continuous position control of a prosthetic. In other words, the present teachings can be used to process nerve signals and control a prosthetic through a range of flexion positions, as opposed to discrete prosthetic positions or states, such as a flexed or extended state.

Non-limiting Discussion of Terminology

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

As used herein, the term circuitry may refer to, be part of, or include: an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term circuitry may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple circuitries may be executed using a single (shared) processor. In addition, some or all code from multiple circuitries may be stored by a single (shared) memory. The term group, as used above, means that some or all code from single circuitry may be executed using a group of processors. In addition, some or all code from single circuitry may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The headings (such as "Background" and "Summary") and sub-headings used herein are intended only for general organization of topics within the present disclosure, and are not intended to limit the disclosure or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all patents and patent applications referenced or cited in this disclosure are incorporated by reference herein.

The description and specific examples, while indicating features and embodiments, are intended for purposes of illustration only and are not intended to limit the scope of the disclosure. Moreover, recitation of multiple embodiments having stated features is not intended to exclude other embodiments having additional features, or other embodiments incorporating different combinations of the stated features. Specific examples are provided for illustrative purposes of how to make and use the described methods, systems, and compositions and, unless explicitly stated otherwise, are not intended to be a representation that given embodiments have, or have not, been made or tested.

As used herein, the words "prefer" or "preferable" refer to embodiments that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, the word "include," and its variants, is intended to be non-limiting, such that recitation of items in a list is not to the exclusion of other like items that may also be useful in the methods, systems, materials, compositions, and devices described. Similarly, the terms "can" and "may" and their variants are intended to be non-limiting, such that recitation that an embodiment can or may comprise certain elements or features does not exclude other embodiments that do not contain those elements or features.

Although the open-ended term "comprising," as a synonym of non-restrictive terms such as including, containing, or having, is used herein to describe and claim embodiments of the present disclosure, embodiments may alternatively be described using more limiting terms such as "consisting of" or "consisting essentially of." Thus, for any given embodiment reciting materials, components, or process steps, the present disclosure also specifically includes embodiments consisting of, or consisting essentially of, such materials, components, or processes excluding additional materials, components, or processes (for consisting of) and excluding additional materials, components, or processes affecting the significant properties of the embodiment (for consisting essentially of), even though such additional materials, components, or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. The use of the term "about" with respect to a range, value, or threshold is to be considered in the context of the range, value, or threshold, as understood by one of ordinary skill in the art. To the extent, the range, value, or threshold cannot be determined from the context, the use of the term "about" can correspond to a ten to fifteen percent range. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A method comprising:
receiving, with processing circuitry of an implant device, an electrical signal from a free tissue graft surgically attached to a portion of a nerve of a subject, wherein the electrical signal is received through an electrode that is implanted inside of the free tissue graft and in electrical communication with the free tissue graft, the free tissue graft being surgically attached to the subject such that the free tissue graft is entirely surrounded by and in direct contact with non-grafted tissue of the subject, wherein the free tissue graft is an autograft of tissue that is harvested from the subject, devascularized, and deinnervated prior to being surgically attached to the subject, wherein the portion of the nerve has reinnervated the free tissue graft, and wherein the electrical signal from the free tissue graft has a voltage amplitude of greater than or equal to about 150 microvolts; and
storing, with the processing circuitry, signal data corresponding to the electrical signal from the free tissue graft in a memory accessible to the processing circuitry.

2. The method of claim 1, further comprising:
generating, with the processing circuitry, the signal data corresponding to the electrical signal from the free tissue graft by conditioning and extracting features from the electrical signal from the free tissue graft.

3. The method of claim 2, further comprising:
decoding, with the processing circuitry, the signal data to predict a movement indicated by the signal data; and
controlling, with the processing circuitry, a prosthetic device based on the prediction.

4. The method of claim 3, wherein the decoding with the processing circuitry utilizes at least one of a classifier and a regression analysis based on previously received training data generated during a calibration process.

5. The method of claim 2, further comprising:
decoding, with the processing circuitry, the signal data to determine whether the signal data corresponds to pathological pain signals; and
generating, with the processing circuitry, an inhibitory stimulus signal when the signal data corresponds to pathological pain signals.

6. The method of claim 2, further comprising:
decoding, with the processing circuitry, the signal data to determine whether the signal data corresponds to pathological bladder contraction signals; and
generating, with the processing circuitry, an inhibitory stimulus signal when the signal data corresponds to pathological bladder contraction signals.

7. The method of claim 1, further comprising:
receiving, with the processing circuitry, pressure signal data from a pressure sensor of a prosthetic device;
generating, with the processing circuitry, a stimulus signal corresponding to the pressure signal data; and stimulating, with the processing circuitry, the portion of the nerve with the stimulus signal through the electrode implanted inside of the free tissue graft and in electrical communication with the free tissue graft.

8. The method of claim 1, further comprising:
communicating, with communication circuitry in communication with the processing circuitry, the signal data to a computing device external to the implant device.

9. The method of claim 1, wherein the voltage amplitude of the electrical signal from the free tissue graft is greater than or equal to about 250 microvolts.

10. The method of claim 1, wherein the electrical signal from the free tissue graft has a signal-to-noise ratio greater than or equal to 4.

11. A method of amplifying a nerve signal in a subject, comprising:
disposing a portion of a nerve within a free tissue graft and securing the portion of the nerve therein, the free tissue graft being an autograft of tissue that is harvested from the subject, devascularized, and deinnervated prior to being surgically attached to the subject;
surgically attaching the free tissue graft directly to the subject such that the free tissue graft is entirely surrounded by and in direct contact with non-grafted tissue of the subject;
implanting inside of the free tissue graft at least one electrode for electrical communication with the nerve, wherein the portion of the nerve regenerates within the free tissue graft so that the nerve produces an electrical signal having a voltage amplitude of greater than or equal to about 150 microvolts without any external electrical input; and
wherein the electrical signal is received by processing circuitry of an implant device through the at least one electrode, the processing circuitry storing signal data corresponding to the electrical signal in a memory accessible to the processing circuitry.

12. The method of claim 11, further comprising cutting the portion of the nerve in the subject.

13. The method of claim 12, wherein the cutting comprises forming a plurality of branches of the nerve, wherein the disposing and introducing are repeated for each respective branch of the plurality.

14. The method of claim 11, wherein the tissue is muscle tissue.

15. The method of claim 11, wherein a maximum dimension of the free tissue graft is less than or equal to about 10 cm.

16. The method of claim 11, wherein a maximum dimension of the free tissue graft is less than or equal to about 5 cm.

17. The method of claim 11, wherein the at least one electrode has a maximum thickness of less than or equal to about 5 mm.

18. The method of claim 11, further comprising stimulating the portion of the nerve with a stimulus signal delivered through the at least one electrode in electrical communication with the free tissue graft.

\* \* \* \* \*